(12) United States Patent
 Radmer et al.

(10) Patent No.: US 8,992,484 B2
(45) Date of Patent: Mar. 31, 2015

(54) DEVICE FOR INJECTING APPORTIONED DOSES OF LIQUID DRUG

(75) Inventors: Bo Radmer, Hillerød (DK); Kristian Glejbøl, Glostrup (DK); Jonas Torry-Smith, Virum (DK); Tom Hede Markussen, Bagsværd (DK); Lars Morten Bom, Herlev (DK); Christian Peter Enggaard, Vejby (DK); Sara Juana Niemann, Bagsværd (DK); Martin Ebro, Albertslund (DK)

(73) Assignee: Novo Nordisk A/S, Bagsvaerd (DK)

( * ) Notice: Subject to any disclaimer, the term of this patent is extended or adjusted under 35 U.S.C. 154(b) by 376 days.

(21) Appl. No.: 12/842,337

(22) Filed: Jul. 23, 2010

(65) Prior Publication Data

US 2011/0046565 A1    Feb. 24, 2011

Related U.S. Application Data

(63) Continuation of application No. 12/864,279, filed as application No. PCT/EP2009/050797 on Jan. 23, 2009, now Pat. No. 8,348,905.

(60) Provisional application No. 61/027,099, filed on Feb. 8, 2008.

(30) Foreign Application Priority Data

Jan. 23, 2008   (EP) ..................................... 0815033

(51) Int. Cl.
    *A61M 5/00*   (2006.01)
    *A61M 5/24*   (2006.01)
    *A61M 5/20*   (2006.01)
    *A61M 5/31*   (2006.01)
    (Continued)

(52) U.S. Cl.
    CPC . *A61M 5/24* (2013.01); *A61M 5/20* (2013.01);
    *A61M 5/3146* (2013.01); *A61M 5/31541*
    (2013.01); *A61M 5/31551* (2013.01); *A61M
    5/31555* (2013.01); *A61M 5/3156* (2013.01);
    *A61M 5/31563* (2013.01); *A61M 5/31575*
    (2013.01); *A61M 5/3158* (2013.01); *A61M
    5/3213* (2013.01); *A61M 2005/2073* (2013.01);
    *A61M 2005/2407* (2013.01); *A61M 2005/3104*
    (2013.01); *A61M 2205/581* (2013.01); *A61M
    2205/583* (2013.01)
    USPC ........................................................ 604/207

(58) Field of Classification Search
    USPC .......................... 604/207, 208, 209, 210, 211
    See application file for complete search history.

(56) References Cited

U.S. PATENT DOCUMENTS 4,475,905 A     10/1984  Himmelstrup
4,592,745 A *    6/1986  Rex et al. ...................... 604/211
(Continued)

FOREIGN PATENT DOCUMENTS

CN    1035055 A    8/1989
EA    007292       8/2006
(Continued)

*Primary Examiner* — Nicholas Lucchesi
*Assistant Examiner* — Shefali Patel
(74) *Attorney, Agent, or Firm* — Wesley A. Nicolas; Reza Green; Richard W. Bork

(57) ABSTRACT

An injection device including a dose setting assembly, and an injection assembly, wherein operating the dose setting assembly to set a dose causes an engagement element to pass a tooth on a toothed rod in a combined translational and rotational movement.

17 Claims, 20 Drawing Sheets

(51) Int. Cl.
   *A61M 5/315*   (2006.01)
   *A61M 5/32*    (2006.01)

(56) References Cited

U.S. PATENT DOCUMENTS

| | | | |
|---|---|---|---|
| 4,973,318 | A | 11/1990 | Holm et al. |
| 5,104,380 | A | 4/1992 | Holman et al. |
| 5,320,609 | A | 6/1994 | Haber et al. |
| 5,674,204 | A | 10/1997 | Chanoch |
| 6,056,728 | A | 5/2000 | von Schuckmann |
| 6,193,698 | B1 | 2/2001 | Kirchhofer et al. |
| 6,726,661 | B2 | 4/2004 | Munk et al. |
| 7,112,187 | B2 | 9/2006 | Karlsson |
| 7,195,616 | B2 | 3/2007 | Diller et al. |
| 7,302,948 | B2 | 12/2007 | Anderson |
| 7,445,613 | B2 | 11/2008 | Hommann |
| 2007/0129687 | A1 * | 6/2007 | Marshall et al. .............. 604/207 |
| 2007/0135767 | A1 | 6/2007 | Gillespie et al. |

FOREIGN PATENT DOCUMENTS

| | | |
|---|---|---|
| EA | 007763 | 12/2006 |
| EP | 338806 A2 | 10/1989 |
| EP | 327910 | 4/1992 |
| EP | 730876 A2 | 9/1996 |
| EP | 1231960 A1 | 8/2002 |
| EP | 1304129 | 4/2003 |
| JP | 4-256758 B2 | 4/2009 |
| WO | WO9710865 | 3/1997 |
| WO | 97/36625 A1 | 10/1997 |
| WO | WO9903520 | 1/1999 |
| WO | WO02053214 | 7/2002 |
| WO | 03/020347 A2 | 3/2003 |
| WO | 03080160 | 10/2003 |
| WO | WO2005039676 | 5/2005 |
| WO | 2007/134954 | 11/2007 |
| WO | 2007/138299 A1 | 12/2007 |
| WO | WO2008116766 | 10/2008 |

* cited by examiner

Fig. 9
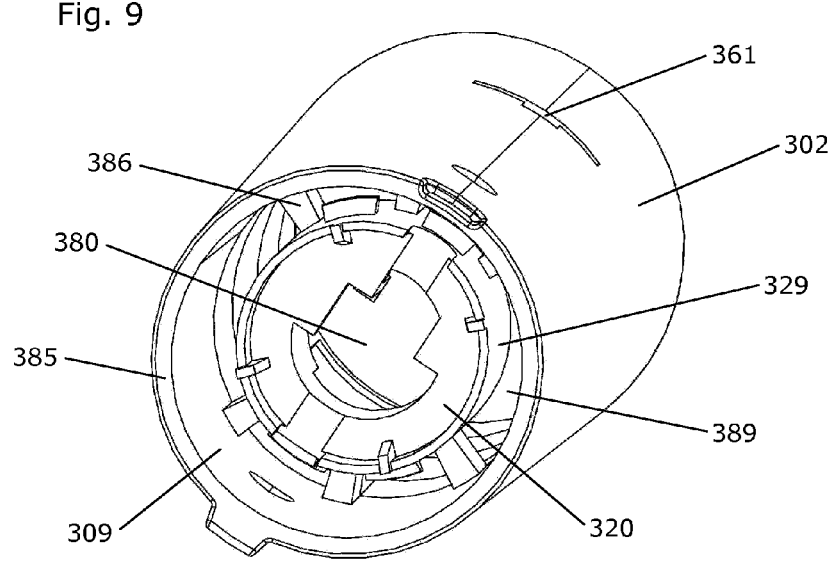
Fig. 10a
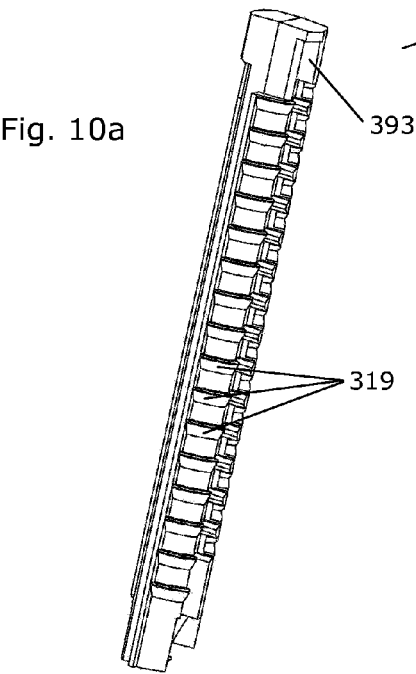
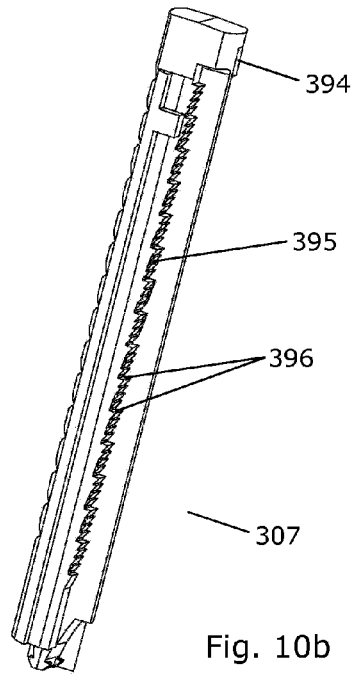
Fig. 10b

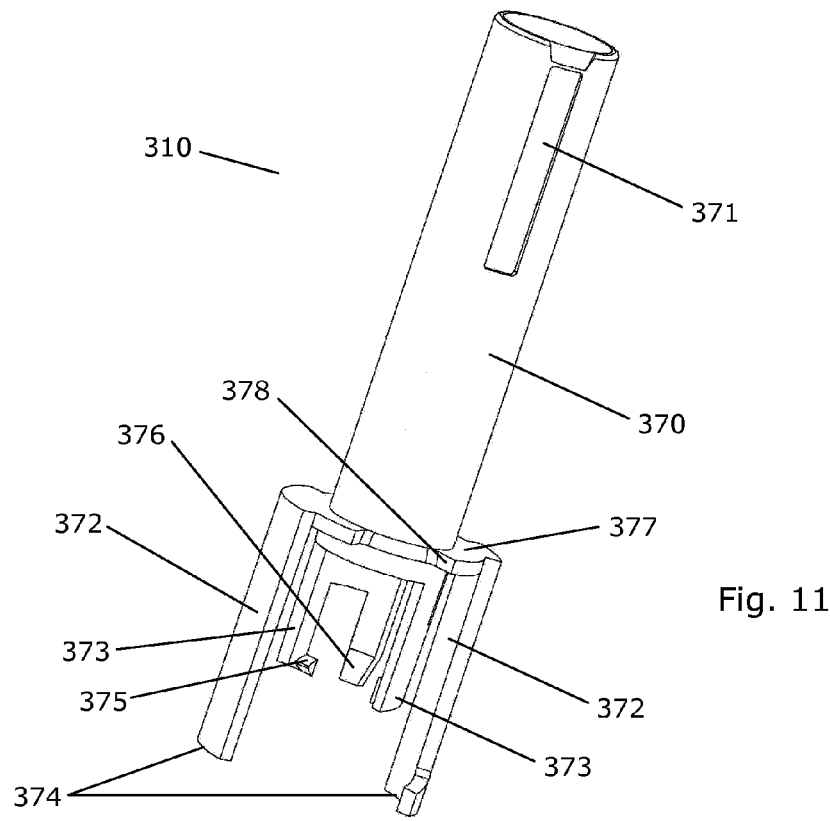
Fig. 11
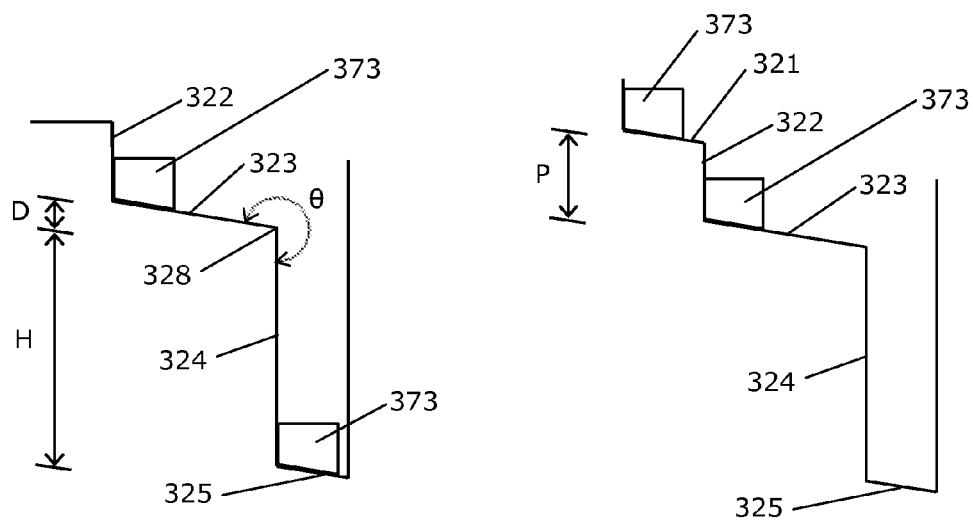
Fig. 12
Fig. 13

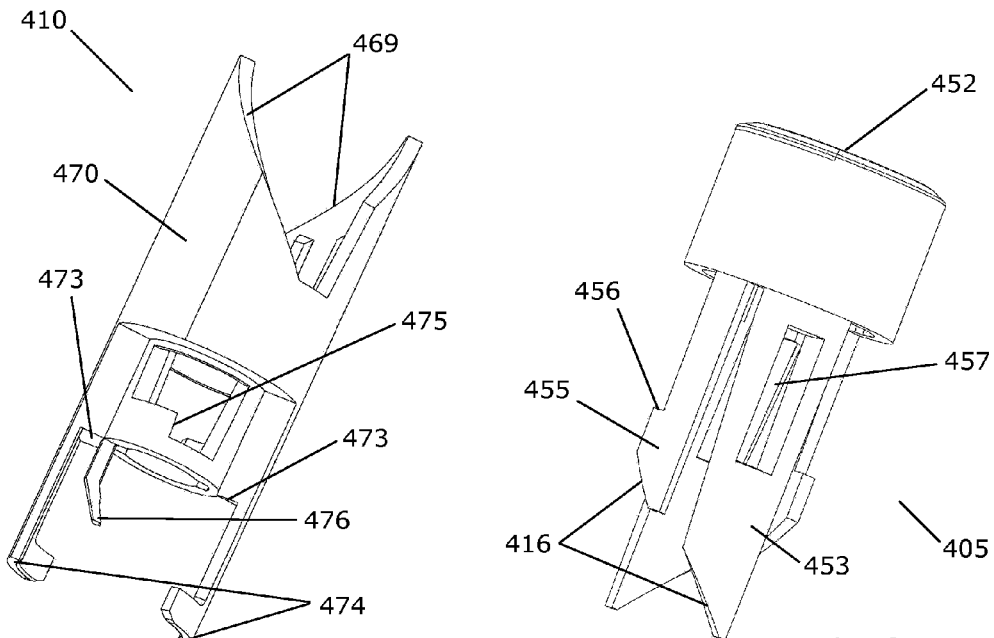
Fig. 24
Fig. 25
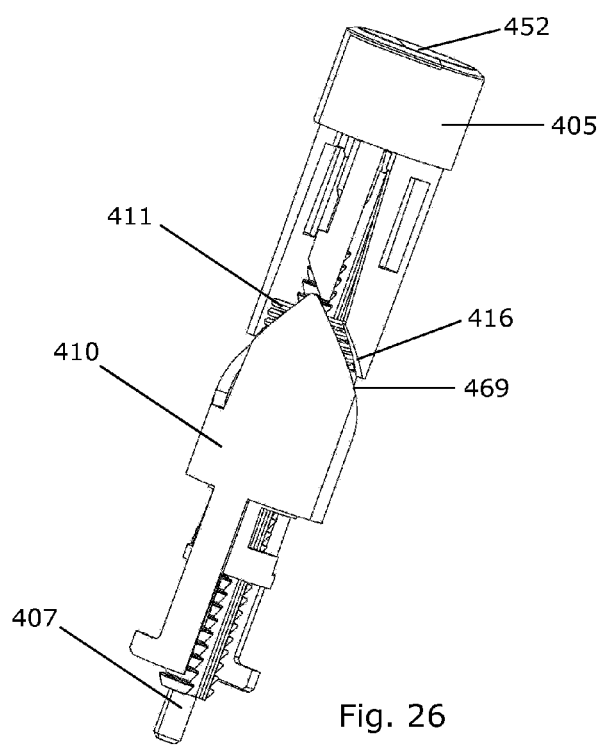
Fig. 26

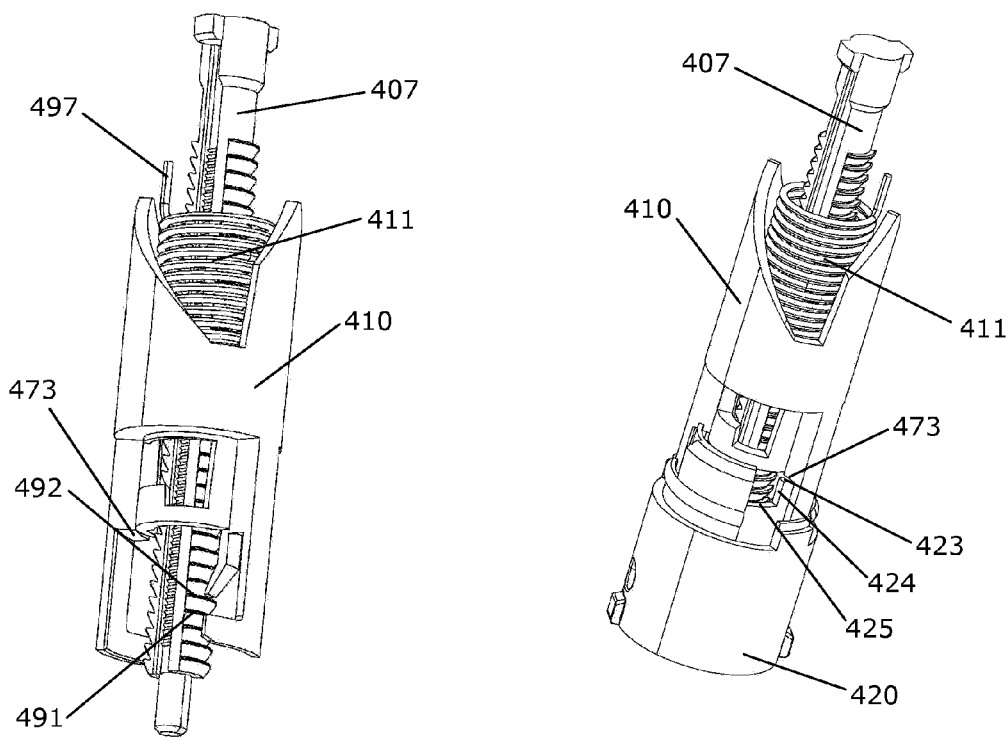
Fig. 27
Fig. 28
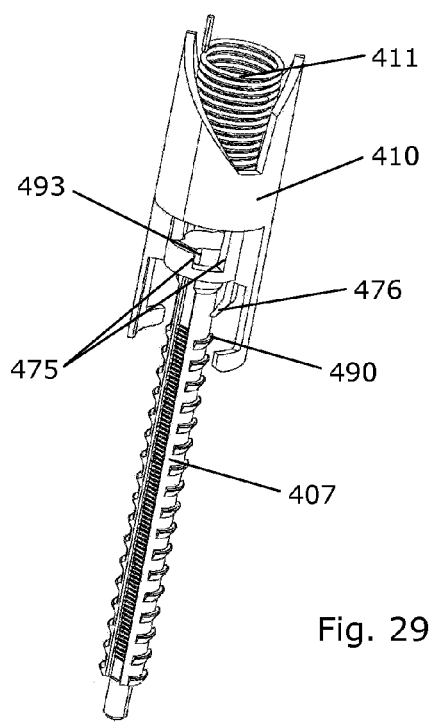
Fig. 29

DEVICE FOR INJECTING APPORTIONED DOSES OF LIQUID DRUG

CROSS-REFERENCE TO RELATED APPLICATIONS

This application is a continuation of U.S. application Ser. No. 12/864,279, filed Jul. 23, 2010, which is a 35 U.S.C. §371 national stage application of International Patent Application PCT/EP2009/050797 (published as WO 2009/092807), filed Jan. 23, 2009, which claimed priority of European Patent Application 08150533.1, filed Jan. 23, 2008; this application further claims priority under 35 U.S.C. §119 of U.S. Provisional Application 61/027,099, filed Feb. 8, 2008.

FIELD OF THE INVENTION

The present invention relates to an injection device for injecting apportioned doses of liquid drug, such as for injecting doses of a single fixed amount of drug, or for injecting doses of a limited number of different amounts of drug. More particularly, the present invention relates to an injection device in which the number of operations to be performed by a user is minimised. The injection device is particularly suitable for self-injection by the user of a liquid drug, e.g. insulin for treating diabetes.

BACKGROUND OF THE INVENTION

Within some therapy areas the tendency of a patient to adhere to the prescribed therapy is dependent on the simplicity of the specific treatment regimen. For example, many people with type 2 diabetes are diagnosed with the disease at a relatively high age where they are less prone to accept a treatment that intervenes too much with their normal way of living. Most of these people do not like constantly being reminded of their disease and, as a consequence, they do not want to be entangled in complex treatment patterns or waste time on learning to operate cumbersome delivery systems.

Basically, people with diabetes need to keep track of, and minimise, their glucose excursions. Insulin is a well-known glucose lowering agent which has to be administered parenterally to be effective in the body. The presently most common way of administering insulin is by subcutaneous injections. Such injections have previously been performed using a vial and a syringe, but in recent years so-called injection devices, or injection pens, have gained more and more attention in the marketplace. This is for one thing due to the fact that for many people these injection devices are easier to handle, particularly as they do not require the user to carry out a separate filling procedure before each injection.

In some prior art injection devices which are suitable for self-injection, the user has to set a desired dose using a dose setting mechanism of the injection device and subsequently inject the previously set dose using an injection mechanism of the injection device. In this case the dose is variable, i.e. the user must set a dose which is suitable in the specific situation each time a dose is to be injected.

Other prior art injection devices are adapted to inject a fixed dose each time it is operated. In this case the user has to prepare the injection device, thereby setting the fixed dose, using a dose setting or loading mechanism, and subsequently inject the dose using an injection mechanism.

U.S. Pat. No. 4,973,318 discloses a disposable syringe comprising a protective cap which is removably mounted over a first housing element of the syringe. The cap is configured to abut a second housing element while mounted in place on the first housing element. The protective cap is engaged with the first housing element such that rotation of the cap with respect to the second housing element causes rotation of the first housing element with respect to the second housing element. This relative rotation causes a variable dose to be set, i.e. the protective cap is used when setting a dose. However, it is necessary for the user to perform the step of setting a dose as well as the step of injecting the set dose.

U.S. Pat. No. 5,674,204 discloses a medication delivery pen having a medication cartridge, a pen body assembly and a cap. The pen body assembly includes a dose setting mechanism and a dose delivery mechanism that are selectively disconnected and connected by attaching and removing, respectively, the cap of the medication delivery pen. When the cap is attached to the medication delivery pen the user can easily dial in and correct the dialled in dosage and when the cap is removed the medication delivery pen is ready to dispense the dialled in dose. Thus, attaching/removing the cap to/from the medication delivery pen causes a clutch mechanism to be operated to switch the medication delivery pen between a dose setting mode and an injection mode. Also in this device it is necessary for the user to perform the step of setting a dose as well as the step of injecting the set dose.

An example from another medical device area, U.S. Pat. No. 7,302,948 discloses a nasal applicator in which a drug container is able to slide back and forth in response to the cocking and actuation of a spring. The drug container is slided backwards when a cap is attached to the nasal applicator. An abrupt stop during the forward movement of the drug container causes a piston to move and eject a dose of the drug through a dispensing nozzle.

U.S. Pat. No. 6,056,728 discloses an injection device which offers automatic needle insertion. It includes an intermediate chamber between the drug reservoir and the injection outlet for receiving a volume of the drug during preparation of the device for injection. The device has a rather bulky construction which makes it less attractive to carry around in e.g. a handbag.

It is desirable to provide an injection device which is simple to handle and which is intuitive and easy for the patient to learn how to use. In particular, it is desirable to provide an injection device which is capable of administering a number of doses of liquid drug, while at the same time requiring a minimum number of operations to be performed by the user. It is also desirable to provide an injection device which clearly indicates to the user when it is ready for injection and when the remaining volume of drug in the reservoir is insufficient to provide a full dose, and which then automatically renders further activation of the injection mechanism impossible. It is further desirable to provide an injection device which has a non-bulky design, so the user is not tempted to leave it at home instead of carrying it along during the day.

Some prior art injection devices offer so-called automatic delivery. These injection devices use energy from an internal energy source, typically a spring, to advance the piston in the reservoir. Automatic injection devices intend to reduce the force required by the user to eject the drug out of the reservoir. An example of such an injection device is found in U.S. Pat. No. 5,104,380.

In an automatic, spring-powered injection device where an engagement member is retracted axially along a toothed piston rod when the device is readied for injection, it must be ensured that the spring is cocked and secured against release at the same time as the engagement member moves into engagement with a dedicated tooth on the piston rod. If the engagement member has moved into engagement with a tooth on the piston rod but the spring has not been secured against release, the device will deliver an unintended dose. On the other hand, if the spring has been cocked and secured against release without the engagement member having moved into engagement with a tooth on the piston rod, no dose will be delivered when the injection mechanism is activated.

It is therefore desirable to provide an automatic injection device with which the user is ensured that a dose is either set correctly, and secured against delivery until the user activates the injection mechanism, or not set at all.

In U.S. Pat. No. 6,193,698 a spring is used to bias a dosing button and a drive arrangement towards a proximal position in an injection apparatus. During an injection the dosing button and the drive arrangement are pushed towards a distal position. To prevent uncontrolled injections, a locking member prevents return movement of the dosing button and the drive arrangement against the biasing force of the spring. In order to release the dosing button the user must manually press a trigger button which is accessible only after manual placement of two sleeves in a "zero" position relative to each other.

It is desirable to provide an injection device which locks the dosing button in a distal position following an injection, and which automatically releases the dosing button and moves it axially back into a proximal position when the injection device is readied for an injection so the user can see that the device is handled properly.

EP 1 304 129 discloses an injection device which includes a mechanism for automatically locking out the dose dial from an inadvertent injection after the dial has been retracted to set a dose. The lockout mechanism comprises an interference fit between flexible fingers formed in the dial and a groove in the device housing. These fingers must be able to withstand large compressive forces in order to prevent the dial from being depressed in case of misuse or accidental handling of the device.

US 2007/0135767 discloses another example of an injection device which includes a mechanism for preventing inadvertent depression of an injection button.

It is desirable to provide an injection device which the user does not risk inadvertently activating to eject a dose of drug while the protective cap is still on and which at the same time does not require a mechanical lock that is able to resist large forces.

It is further desirable to provide an injection device which is both safe and effective to use and safe to carry around.

Generally, when manufacturing injection devices which comprise a piston rod adapted to move a piston in a reservoir to thereby expel drug out of the reservoir it is essential that the piston rod is in engagement with the piston during the entire course of injection. If this is not the case the user may risk injecting a smaller amount of drug than intended. However, it is for several reasons preferred that the drug is not pressurised in the reservoir when the user takes the injection device into use for the first time. Injection devices are therefore often manufactured in such a way that a small clearance is deliberately provided between the piston rod and the piston to allow some play of the piston rod during transportation. In case of variable dose injection devices, when taking the device into use for the first time, the user sets a small dose and ejects it into the air. This action primes the injection device such that when a next dose is set the user is sure to inject the correct amount of drug, since the piston rod and the piston are now connected. In some fixed dose injection devices the piston rod travels a substantial distance each time a dose is injected. If the user in this case initially sets a dose and fires it into the air to prime the device, a substantial amount of drug may be wasted to the surroundings. This is particularly unwanted if the drug is expensive.

It is therefore desirable to provide a fixed dose injection device with which a user can perform an initial priming without wasting an approximately full dose of drug.

SUMMARY OF THE INVENTION

It is an object of the invention to provide an injection device in which the number of operating steps required to be performed by the user is reduced as compared to similar prior art injection devices.

It is a further object of the invention to provide an injection device which is intuitive and thereby easy to learn how to use.

It is an even further object of the invention to provide an injection device in which the dose setting procedure is simplified as compared to similar prior art injection devices.

It is an even further object of the invention to provide an injection device which clearly signals to the user when it is ready for an injection.

It is an even further object of the invention to provide an injection device which clearly signals to the user when the remaining amount of medicament in the reservoir is insufficient to provide another full dose and which automatically renders further use of the device impossible.

It is an even further object of the invention to provide an injection device in which the injection means is automatically disabled when the protective cap is mounted on the device and automatically enabled when the protective cap is dismounted from the device, thereby ensuring that the user do not risk involuntarily ejecting a dose of medicament into the cap when for example carrying the device in a hand bag.

It is an even further object of the invention to provide an injection device which automatically sets a correct dose, thereby eliminating the risk of a user setting an incorrect dose.

It is an even further object of the invention to provide an injection device which is capable of injecting a predetermined dose and which has an initial priming feature allowing the user to perform a first shot with the injection device that results in an ejection of a smaller volume of drug than the predetermined dose.

In the following disclosure of the present invention, aspects and embodiments will be described which address one or more of the above objects or which address objects apparent from the disclosure as well as from the description of exemplary embodiments.

Thus, according to a first aspect of the invention a mechanical injection device for injecting apportioned doses of liquid drug is provided, the injection device comprising dose setting means being operable to set a dose, injection means being operable to inject a previously set dose, a removable cap, and a cap receiving part adapted to abut or engage with the cap when the cap is mounted on the injection device, wherein the dose setting means is operatively coupled to the cap receiving part in such a manner that mounting and/or dismounting of the cap on/from the injection device causes the dose setting means to set a dose.

The injection device may for example be of the kind which is able to repeatedly set and deliver a predetermined dose.

In the present context the term 'mechanical injection device' should be interpreted to mean an injection device which is mechanically operated as opposed to motor driven injection devices.

In the present context the term 'liquid drug' should be interpreted to mean a drug in a liquid state, such as, e.g., a solution or a suspension.

In the present context the term 'predetermined dose' should be interpreted in such a manner that when the dose setting means is operated a specific fixed dose is set, i.e. it is not possible to set an arbitrary dose. However, the predetermined dose may be variable in the sense that it may be possible to initially set the injection device to a selected dose, and the dose setting means will then set this selected dose each time the dose setting means is operated. It should also be noted that the term 'predetermined dose' does not rule out that the injection device has a priming function.

The injection device is preferably capable of injecting multiple doses of liquid drug.

The dose setting means is the part of the injection device which is operated when a dose is being set. Similarly, the injection means is the part of the injection device which, when operated, is causing a set dose to be injected. The injection means often comprises a movable piston rod being adapted to cooperate with a piston arranged in a cartridge containing the liquid drug in such a manner that operation of the injection means causes the piston rod to move in such a manner that the piston is moved inside the cartridge in a direction which causes liquid drug to be expelled from the cartridge via a needle arranged to penetrate a septum of the cartridge.

The injection device comprises a removable cap which may be adapted to cover a needle holding part of the injection device when the injection device is not in use. Thereby the removable cap is capable of protecting a needle mounted on the needle holding part, preventing needle sticks and preventing accidental spilling of liquid drug. The cap can be removed when it is desired to inject a dose, thereby uncovering the needle holding part.

The cap receiving part is a part of the injection device which is adapted to receive and hold the removable cap when it is mounted on the injection device. It may comprise means for retaining the cap, such as a bayonet joint, a threaded portion, a snap lock, etc. The cap receiving part may be adapted to receive the cap when the cap is mounted on the injection device to cover the distal part of the injection device. Alternatively, the cap receiving part may be adapted to receive the cap when the cap is mounted on the proximal part of the injection device.

The dose setting means is operatively coupled to the cap receiving part, i.e. performing specific operations of the cap receiving part affects the dose setting means. More particularly, the dose setting means and the cap receiving part are coupled in such a manner that mounting and/or dismounting of the cap on/from the injection device causes the dose setting means to set a dose. The dose setting means and the cap receiving part may be mechanically coupled, either directly or via one or more intermediate parts, or they may be coupled in any other suitable way as long as specific operations of the cap receiving part affects the dose setting means in such a manner that the dose is set. Thus, the dose may be set when the cap is mounted or when the cap is dismounted. Alternatively, the dose may be partly set when the cap is mounted, the remaining part of the dose being set when the cap is subsequently dismounted. In any event, performing a cycle of operations comprising mounting and dismounting the cap results in the dose being set by the dose setting means, preferably automatically.

The removable cap is normally positioned at the cap receiving part, preferably covering a needle holding part or a jet orifice, when the injection device is not in use, and the cap is removed when it is desired to inject a dose of drug by means of the injection device. After the dose has been injected the cap is once again mounted at the cap receiving part. Thus, each time a dose is injected the cap has been mounted and dismounted since the previous dose was injected. Since the dose setting means and the cap receiving part are coupled as described above, such a mounting/dismounting cycle of the cap automatically results in a dose being set. Therefore, when the user has removed the cap in order to inject a dose, the dose is already set, and it is not necessary for the user to perform additional operating steps in order to set the dose. Thereby the number of steps to be performed by the user is reduced. Furthermore, since the dose is automatically set, the risk of introducing errors during dose setting is reduced.

Thus, in one particular embodiment of the invention an injection device for administering apportioned doses of a liquid drug is provided, the injection device comprising dose setting means operable to set a dose, injection means operable to inject the set dose, a removable cap, a cap receiving part adapted to abut or engage with the cap when the cap is mounted on the injection device, wherein the dose setting means is operatively coupled to the cap receiving part in such a manner that mounting and/or dismounting of the cap on/from the injection device causes the dose setting means to set a single dose.

In the present context, the term 'to set a single dose' should be interpreted as outlined in the above, i.e. mounting the cap on, or dismounting the cap from, the injection device causes the dose setting means to set one dose which is deliverable upon operation of the injection means. By such an arrangement it is therefore not possible to inject two consecutive doses without performing a cycle of mounting and dismounting the cap on/from the injection device. This constitutes a safety feature of the device since if it was possible to inject a multiple number of doses, such as the same dose a multiple number of times, without performing the cap mounting/dismounting cycle, the user would have to keep count of how many times the injection means had been operated. This could lead to confusion and uncertainty regarding the actual dose delivered.

A substantially linear movement of the cap may cause the dose setting means to set the dose, i.e. the movement of the cap may involve a substantially linear translation which causes the dose setting means to set the dose. According to this embodiment, the cap is mounted and/or dismounted in a substantially linear movement. In this case the cap is preferably retained in the mounted position by means of a snap lock, a bayonet joint or the like. According to this embodiment, the cap may move an element in a substantially axial direction when it is mounted or dismounted. The movement of the element may cause the dose to be set, e.g. by storing energy in a spring member and/or by moving an injection button in an axial direction.

Alternatively, or additionally, a rotational movement of the cap may cause the dose setting means to set the dose, i.e. the movement of the cap may involve a rotational movement which causes the dose setting means to set the dose. According to this embodiment, the cap is preferably mounted and/or dismounted in a movement which is at least partly rotational, e.g. a purely rotational movement or a spiralling movement. The cap may, in this case, be retained at the cap receiving part by means of a threaded connection, a bayonet joint or the like. The rotational part of the movement may alone be responsible for setting of the dose, e.g. by causing an element of the injection device to rotate along. For instance, in the case that the cap is retained by means of a bayonet joint, the rotating part of the mounting or dismounting operation may cause an element to rotate along. It may be envisaged that the cap is mounted in a substantially linear movement, pressing the cap past a threaded portion, and that the cap must be rotated along the threaded portion in order to dismount the cap. In this case the rotating part of the dismounting movement may advantageously cause the dose to be set. This has the advantage that the dose is not set until immediately prior to the intended injection of the dose, and it can thereby be avoided that a loaded injection device must be carried in a pocket or a handbag. Thereby the risk of accidentally ejecting the set dose prematurely in the cap is minimised. However, this could alternatively be obtained by means of a suitable locking mechanism preventing injection of the set dose until the cap has been removed.

As an alternative to the purely rotational movement, a combination of a linear and a rotational movement, i.e. a spiralling movement may cause the dose setting means to set the dose.

In a particular embodiment of the invention, mounting the cap on the injection device causes an element to move axially with respect to the piston rod to thereby move an engagement member along the piston rod to a more proximal position. Each time a dose is set by mounting the cap on the injection device the engagement member is thus moved further along the piston rod towards the proximal end thereof.

In an exemplary embodiment of the invention an injection device for administering apportioned doses of a liquid drug is provided, the injection device comprising a proximal part and an opposite distal part, a cartridge adapted to hold the liquid drug and comprising a movable piston, dose setting means operable to set a dose, injection means operable to inject the set dose and comprising a piston rod adapted to sequentially advance the piston in the cartridge, each sequential advancement corresponding to the set dose, a removable cap adapted to cover the distal part of the injection device, and a cap receiving part adapted to abut or engage with the cap when the cap is mounted on the injection device, wherein the dose setting means is operatively coupled to the cap receiving part in such a manner that mounting and/or dismounting of the cap on/from the distal part of the injection device causes the dose setting means to set a dose. Since the distal part of the injection device is the part from which the drug is ejected out of the reservoir, the removable cap is adapted to cover and protect the drug outlet.

The injection device may further comprise energy means connected to the dose setting means and the injection means in such a manner that energy is stored in the energy means during setting of a dose, and in such a manner that previously stored energy is released from the energy means during injection of a dose, thereby causing the dose to be injected. The energy means may be a spring member which may be adapted to be loaded along its centre axis, e.g. by compressing the spring or elongating the spring. The spring member may be a compressible spring or a torsion spring. In the case that the spring member is a compressible spring, the injection device may advantageously be operated in the following manner. When the cap is either mounted on or dismounted from the cap receiving part a spring compressing element is moved, preferably in an axial direction, thereby compressing the spring. The spring compressing element is locked in this position, thereby retaining the spring member in the compressed state. When the injection needle has been inserted at a desired injection site, the injection button is pressed. This causes the spring compressing element to be moved out of the locked position, and the energy stored in the spring is thereby released in such a manner that it causes a piston rod to move while pressing a piston of a cartridge forward, thereby causing a dose of drug to be injected from the cartridge, via the injection needle.

According to a second aspect of the invention an injection device is provided comprising a housing, dose setting means operable to set a dose, injection means operable to inject the set dose and comprising an at least partly toothed rod, a drive member adapted to undergo relative motion with respect to the toothed rod when the dose setting means is operated and to transmit a driving force to the toothed rod when the injection means is operated, the drive member comprising an engagement element adapted to engage with the toothed rod, guiding means adapted to guide the movement of the drive member and/or the toothed rod, and energy means operatively coupled to the dose setting means and the injection means and adapted to store and release energy for translational and rotational motion.

The drive member may be coupled with the energy means in such a manner that movement of the drive member causes the energy means to store and/or release energy and, conversely, in such a manner that release of energy from the energy means causes the drive member to move. The energy means may comprise a compression spring being rotationally pre-stressed to bias the drive member in a specific rotational direction.

When the dose setting means is operated to set a dose the drive member will undergo a relative motion with respect to the toothed rod whereby the engagement element will be moved out of engagement with a tooth on the toothed rod and moved along the toothed rod to pass a more proximally positioned tooth. This relative motion is guided by the guiding means. The guiding means may form part of the housing or may be a separate element coupled to the housing. When the injection means is subsequently operated to inject the set dose the engagement member will engage the tooth it just passed and the drive member will move distally in the housing while slaving the toothed rod. Also this motion is guided by the guiding means.

Hence, in the present context the term 'the dose setting means is operated to set a dose' should be interpreted to mean that the dose setting means is operated to a degree where a dose is actually set. Just operating the dose setting means does not necessarily lead to a dose being set, as will be clear from the below.

Further, in the present context the term 'tooth' should be interpreted to mean any lateral structural irregularity on the rod, such as e.g. a protrusion or an indentation, capable of receiving an engagement element and allowing for a mutual axial displacement of the rod and the engagement element.

In an exemplary embodiment of the invention the guiding means comprises a structure which enables the drive member and the toothed rod to perform a purely translational relative motion during one part of the relative motion and to perform a combined translational and rotational relative motion during another part of the relative motion. In this particular embodiment the guiding means is provided with a longitudinal first guiding surface which is substantially parallel with the toothed rod and which enables the purely translational relative motion between the drive member and the toothed rod. The guiding means is further provided with a sloping second guiding surface which meets the first guiding surface at a transition point and which enables the combined translational and rotational relative motion between the drive member and the toothed rod. The second guiding surface and the first guiding surface are preferably mutually angled between 180° and 270°, more preferably between 225° and 270°, and most preferably between 240° and 270°. In any case the angle between the first guiding surface and the second guiding surface and the traversable dimension of the second guiding surface constitute two parameters which should be fitted so that when the drive member traverses the second guiding surface during dose setting the drive member and the toothed rod perform a combined translational and rotational relative motion during which the engagement element passes a tooth on the toothed rod.

The energy means may comprise a compression spring being rotationally pre-stressed to constantly bias the drive member in a specific rotational direction. The spring may further be axially pre-stressed to constantly bias the drive member in the distal direction of the injection device. This means that when the drive member is traversing the first guiding surface of the guide means it is exposed to the axial force of the spring seeking to displace it distally in the injection device. During dose setting the drive member may thus traverse the first guiding surface against the force of the spring, while during injection the drive member may traverse the first guiding surface under the force of the spring. Further, when the drive member is traversing the first guiding surface it may be exposed to the rotational force of the spring. However, the drive member is prevented from being rotated in accordance with a biasing rotational force of the spring when traversing the first guiding surface. This is due to the first guiding surface being arranged longitudinally and substantially in parallel with the toothed rod.

The transition point denotes the position where the first guiding surface and the second guiding surface meet, i.e. the point where the drive member is transitioned from traversing the first guiding surface to traversing the second guiding surface, and vice versa. When the drive member is traversing the second guiding surface it may be exposed to both the axial and the rotational biasing forces of the spring. Since the second guiding surface is sloped these biasing spring forces enable a combined translational and rotational movement of the drive member with respect to the toothed rod. During dose setting the drive member may traverse the second guiding surface under the rotational force of the spring, but against the axial force of the spring. During operation of the injection means the drive member may traverse the second guiding surface against the biasing rotational force of the spring.

The spring and the sloping angle of the second guiding surface are preferably dimensioned so that the biasing rotational force of the spring is able to move the drive member along the second guiding surface against the biasing axial force of the spring.

The guiding means is preferably provided with an abutting surface adapted to stop the combined translational and rotational movement of the drive member when the drive member is in a position where the engagement element has just passed a tooth on the toothed rod. In this position the spring is both cocked and secured against release since the biasing rotational force of the spring is able to overcome the biasing axial force of the spring and thereby retain the drive member in a stabile stationary state.

The guiding means is further preferably provided with an abutting surface adapted to stop the translational movement of the drive member during injection, thereby indicating an end-of-dose position, i.e. a position of the drive member corresponding to the complete delivery of the set dose. The actual dose delivered may be determined by the distance between two consecutive teeth on the toothed rod. This distance is greater than the axial distance travelled by the drive member along the first guiding surface of the guiding means, but smaller than the total axial distance travelled by the drive member following activation of the injection means, i.e. smaller than the combined axial dimension of the first and the second guiding surfaces. The actual dose delivered may alternatively be determined by the total axial distance, which the drive member travels following activation of the injection means.

The above described arrangement is particularly advantageous since when the user operates the dose setting means to set a dose the last part of the dose setting may be performed automatically by the injection device. This is due to the fact that during the first part of the dose setting the user manually operates the dose setting means to move the drive member proximally along the first guiding surface against the biasing translational force of the spring. If the spring is rotationally pre-stressed it constantly exerts a force on the drive member which may bias the drive member against the first guiding surface. Hence, in this case, as long as the drive member is guided by the first guiding surface it is prevented from rotating and it therefore performs a purely translational movement during which the engagement element is slided along the toothed rod. When the user has forced the drive member so far proximally that it reaches the transition point at the connection between the first guiding surface and the second guiding surface the biasing rotational force of the spring may begin rotating the drive member and force it to travel along the second guiding surface until it reaches the stop at the abutting surface. Since the second guiding surface is sloped the drive member will thereby be performing a combined rotational and translational movement with respect to the toothed rod. The configuration of the first and second guiding surfaces may be such that the axial displacement which the drive member undergoes from the transition point to the stop at the abutting surface moves the engagement element from a position just below, or distally of, a given tooth on the toothed rod to a position just above, or proximally of, the tooth. This ensures that when the injection means is operated the engagement element will be able to move into engagement with this tooth and slave the toothed rod axially towards the distal end of the injection device. During movement of the drive member along the second guiding surface, the spring may release rotational energy while it stores translational energy. In that case, when the drive member reaches the stop at the abutting surface the spring is cocked as well as secured against release until the next activation of the injection means.

As long as the dose setting means is manipulated in such a way that the drive member travels along the first guiding surface no dose is set, and if the user ends the manipulation of the dose setting means before the drive member has reached the transition point the biasing translational force of the spring may just return the drive member to the starting point, i.e. the end-of-dose position. However, when the dose setting means is manipulated to an extent where the drive member reaches the transition point the spring may take control of the remaining part of the dose setting and ensure that the dose is actually being set, i.e. that the engagement element actually passes the intended tooth on the toothed rod, and that the drive member is retained in a stabile stationary state from which it can not be moved unless the injection means is manipulated. In that case, the last part of the dose setting procedure is carried out automatically by the injection device and the user does not have any options of intervention.

When the user operates the injection means to inject the set dose the drive member may be initially forced along the second guiding surface against the biasing rotational force of the spring. At some point during this movement the engagement element will move into engagement with a tooth on the toothed rod. When the drive member reaches the transition point the biasing translational force of the spring may move the drive member and the toothed rod axially in the distal direction until the drive member meets the abutting surface.

The toothed rod may be operatively coupled with a drug containing reservoir in the injection device in such a manner that the axial distance travelled by the toothed rod correlates with the actual dose delivered from the reservoir. The drug containing reservoir may be a rigid reservoir, such as a cartridge, comprising an axially moveable piston and the toothed rod may be operatively coupled to the reservoir via the piston. Alternatively, the drug containing reservoir may be a flexible reservoir which is adapted to undergo a controlled deformation when the toothed rod is moved axially in the injection device. In any case, the axial movement of the toothed rod may cause a volume reduction of the drug containing reservoir corresponding to the delivered dose.

The dose setting means may be operated by pulling the dose button in a proximal direction away from the housing. Alternatively, the dose setting means may be operated as described in the following. The injection device may further comprise a removable cap and a cap receiving part adapted to abut or engage with the cap when the cap is mounted on the injection device. The dose setting means may be operatively coupled with the cap receiving part in such a manner that mounting the cap on the injection device causes the drive member to move axially along the toothed rod while being guided in this movement by the energy means and the geometry of the guiding means, as described above. In this particular embodiment, mounting the cap on the injection device causes the injection device to automatically set a dose. The guiding means may be configured so that each time the cap is mounted on the injection device the drive member travels the same distance proximally and each time the injection means is activated the drive member travels the same distance distally, in which case the injection device is a fixed dose delivery device. However, the guiding means and/or the toothed rod may alternatively, or additionally, be configured so that it is possible to pre-calibrate the zero dose position before a dose setting, thereby in practice providing a variable dose delivery device capable of delivering a limited number of different doses of drug. This could for example be implemented by providing means for regulating the axial dimension of the first guiding surface.

The energy means may comprise a compression spring being rotationally pre-stressed as described above. However, other suitable energy means may be used such as for example two or more springs each being able to provide a part of the energy needed for translational and rotational motion, e.g. a compression spring capable of providing energy for translational motion and a torsion spring capable of providing energy for rotational motion, an axially compressible torsion rod or an arrangement comprising a tension spring.

According to a third aspect of the invention an injection device for administering predetermined doses of liquid drug is provided comprising dose setting means operable to set a dose, injection means operable to inject the set dose and comprising an at least partly toothed rod, and a drive member adapted to undergo relative motion with respect to the toothed rod during dose setting and to transmit a driving force to the toothed rod during injection, wherein the injection device has a priming feature which allows the user to prime the injection device without ejecting an approximately full predetermined dose.

The priming feature may be implemented by providing guiding means as described in connection with the second aspect of the invention, the guiding means further comprising a second longitudinal guiding surface. This second longitudinal guiding surface may be identical to the abutting surface adapted to stop the movement of the drive member along the sloping ramp surface during dose setting. Alternatively, it may be another longitudinal surface being physically connected to the sloping ramp surface. In any case, the second longitudinal guiding surface is preferably connected to a support shelf in such a way that before the user takes the injection device into use for the first time, such as when the injection device is delivered from the manufacturer, the drive member rests on the support shelf and when the user performs the very first operation of the injection means, the drive member is automatically caused to travel the second longitudinal guiding surface to take in a position on the sloping ramp surface. In case the injection device further comprises energy means being operatively coupled to the dose setting means and the injection means and being adapted to store and release energy for translational and rotational motion when the user performs this first operation of the injection means the energy means may be activated to execute the initial movement of the drive member.

The longitudinal dimension of the second longitudinal guiding surface is smaller than the longitudinal dimension of the first guiding surface which guides the drive member between the transition point and the end of dose position. This means that the initial axial movement of the drive member is smaller than the axial movement it undergoes during regular injection. In other words, since the drive member slaves the toothed rod during injection the toothed rod is displaced axially a smaller distance upon the initial activation of the injection means than upon a subsequent activation of the injection means leading to the delivery of a set dose. Thereby it is possible to perform an initial priming of the injection device without wasting an amount of drug approximately equal to a predetermined dose.

The injection device may be provided with a tamper band which the user can pull off to start the priming shot. This tamper band may e.g. be placed at the distal end of the housing or just distally of the injection button. Alternatively to the user pressing the injection button to perform the initial priming, the priming may be activated by turning the injection button clockwise or anti-clockwise a certain number of degrees to remove the slider from the initial shelf position.

According to a fourth aspect of the invention a mechanical injection device for injecting apportioned doses of liquid drug is provided, the injection device comprising dose setting means being operable to set a dose, injection means being operable to inject a previously set dose, an injection button being operatively coupled to the dose setting means and the injection means and being axially moveable between a first position in which a dose is set and the injection device is ready for injection and a second position in which the injection means has been activated to inject the set dose, and retaining means for retaining the injection button in the second position upon activation of the injection means to inject the set dose. When the user removes his/her finger from the injection button after an injection the injection button will thus stay in the second position, thereby signalling to the user that the injection device is not yet ready for another injection.

In the present context the term 'a second position in which the injection means has been activated to inject the set dose' should be interpreted to mean a position where the injection means has been activated to a degree allowing for the complete set dose to be injected.

The injection device comprises a proximal part and an opposite, distal part, and it is preferably of an elongated shape, defining a general axis which in the abstract bridges the proximal part and the distal part. In the present context, an 'axially moveable' or 'axially displaceable' element should thus be interpreted as an element which is moveable or displaceable along the general axis of the injection device.

The retaining means may be operatively coupled to the dose setting means in such a manner that when the dose setting means is operated to set a dose the retaining means is automatically disabled. This will enable the injection button to move from the second position back to the first position. In a particular embodiment, when the dose setting means is operated to set a dose the injection button is automatically moved from the second position to the first position, whereby the injection device signals to the user that it is ready for injection.

The second position may be a position in which the injection button is fully depressed in or against the housing and in which only the top part or the push surface of the injection button can be seen and/or touched by the user. The first position may, conversely, be a position in which the injection button clearly protrudes from the housing. Preferably, the axial distance which the injection button travels between the first position and the second position is sufficiently large to provide a clear indication of whether the injection device is ready for injection or not.

When the dose setting means is operated to set a dose, the injection button may be moved from the second position to the first position by a force transmitting member abutting or engaging with the injection button in such a manner that a translational, rotational or spiralling movement of the force transmitting member causes the movement of the injection button. The injection button may be moved substantially linearly, i.e. non-rotationally, between the first position and the second position. Alternatively, or additionally, the movement may involve a rotation of the injection button.

The retaining means holding the injection button in the second position when the injection means has been activated to inject the set dose may comprise a simple friction fit between the injection button and the housing or the force transmitting member, e.g. between the exterior of the injection button and the interior of the housing. Alternatively, or additionally, the retaining means may comprise a snap fit between the injection button and the housing or the force transmitting member. The injection button may comprise a catch member adapted to engage with a locking geometry on the housing, e.g. on the interior of the housing. Conversely, the housing may be provided with a catch member adapted to engage with a locking geometry on the injection button. During injection when the injection button reaches the second position the catch member moves into engagement with the locking geometry and retains the injection button from reverse movement. During operation of the dose setting means the engagement may be released by another force transmitting member acting to move the catch member away from the locking geometry.

Energy means may act on the injection button to bias the injection button towards the first position. In this case, disabling the retaining means may cause the energy means to automatically release energy for moving the injection button to the first position. In an exemplary embodiment, the energy means comprises a spring being compressed during injection by the movement of the injection button from the first position to the second position. Disabling the retaining means when operating the dose setting means to set a dose causes the spring to push the injection button back to the first position, thereby indicating that a dose has been properly set and that the injection device is ready for injection.

In a particular embodiment an injection device for administering apportioned doses of a liquid drug is provided comprising a reservoir adapted to hold the liquid drug and comprising a moveable piston, dose setting means being operable to set a dose, injection means being operable to inject a previously set dose and comprising a piston rod adapted to sequentially advance the piston in the reservoir, each sequential advancement corresponding to the set dose, an injection button being operatively coupled to the dose setting means and the injection means and being axially moveable between a first position in which a dose is set and the injection device is ready for injection and a second position in which the injection means has been activated to inject the set dose, retaining means for retaining the injection button in the second position upon activation of the injection means to inject the set dose, a removable cap, and a cap receiving part adapted to abut or engage with the cap when the cap is mounted on the injection device, wherein the dose setting means is operatively coupled to the cap receiving part in such a manner that mounting the cap on the injection device causes the dose setting means to substantially simultaneously set a dose, disable the retaining means, and move the injection button from the second position to the first position.

In a further embodiment an injection device is provided comprising a variable volume reservoir, dose setting means operable to set a dose, injection means operable to inject the set dose and comprising a piston rod adapted to cause a volume reduction of the reservoir, a drive member adapted to perform relative translational and rotational motion with respect to the piston rod during dose setting and to transmit a driving force to the piston rod during injection, a removable cap, a cap receiving part adapted to abut or engage with the cap when the cap is mounted on the injection device, an injection button operatively coupled to the dose setting means and the injection means and axially moveable between a first position in which a dose is set and the injection device is ready for injection and a second position in which the injection means has been activated to inject the set dose, and energy means operatively coupled to the dose setting means and the injection means and adapted to store and release energy for translational and rotational motion, wherein the piston rod comprises a structural element adapted to engage with the drive member to prevent the drive member from rotating during operation of the dose setting means when the remaining amount of drug in the reservoir is insufficient to provide another full dose, thereby providing an end-of-contents indication.

By such an arrangement, when the piston has been advanced to a point where an insignificant or insufficient amount of drug is left in the reservoir the drive member is still able to move axially along the piston rod during dose setting, but it is prevented from rotating with respect to the piston rod. In case mounting the cap on the injection device affects the dose setting means by causing the drive member move relative to the piston rod, it is thus still possible to mount the cap on the injection device. However, an axial displacement alone will not cause a dose to be set, and the device is therefore rendered impossible to use for further injections.

As described above, the injection button may be automatically moved from the second position to the first position when the dose setting means is operated to set a dose. However, when the dose setting means is operated without a dose actually being set, the injection button will not move to the first position, and the above arrangement will therefore signal to the user mounting the cap on the cap receiving part after injection of the last dose that no further doses remain in the injection device.

The structural element provided on the piston rod may be a bead, a hammerhead construction or another configuration suited for engagement with the drive member in order to prevent the drive member from rotating relative to the piston rod. In case the piston rod is a toothed rod, the structural element may advantageously be provided at the proximal end of the piston rod, e.g. to rotationally lock the drive member after passage and activation of the most proximally positioned tooth on the piston rod.

According to a fifth aspect of the invention an injection device is provided which comprises a locking mechanism preventing injection of a set dose. Such a locking mechanism is preferably used for preventing that a set dose is accidentally expelled before it is intended to inject the dose, e.g. before a needle or a jet nozzle has been appropriately positioned at a suitable and desired injection site. This is particularly useful in the case that mounting of the cap causes the dose setting means to set a dose, since in this case some time will elapse between setting the dose and injecting it, and it may very well be necessary to carry the injection device along during this time interval, e.g. in a pocket or a handbag.

The locking mechanism may be automatically activated when the cap is mounted on the injection device. According to this embodiment, mounting the cap may advantageously result in setting the dose as well as activating the locking mechanism. Alternatively, the locking mechanism may be manually and/or separately operable, or it may be automatically activated by other suitable actions than mounting the cap.

Thus, according to an exemplary embodiment an injection device for administering apportioned doses of a liquid drug is provided comprising a variable volume reservoir adapted to hold the liquid drug, dose setting means operable to set a dose, injection means operable to inject the set dose, a removable cap, a cap receiving part adapted to abut or engage with the cap when the cap is mounted on the injection device, wherein the injection means is operatively coupled to the cap receiving part in such a manner that mounting the cap on the injection device disables the injection means, thereby preventing an ejection of drug from the reservoir. This type of arrangement is advantageous since the user is prevented from risking inadvertently activating the injection means when e.g. carrying the injection device in a pocket or a handbag.

According to one embodiment, the locking mechanism must be separately switched to an unlocking state prior to injection of a set dose. This may be performed manually and/or separately. Alternatively, the locking mechanism may be automatically switched to the unlocking state when the cap is dismounted. In the case that mounting the cap activates the locking mechanism and dismounting the cap switches the locking mechanism to the unlocking state, the cap may be regarded as forming part of the locking mechanism. This embodiment is very safe, since the locking mechanism is automatically activated and deactivated, and therefore the user does not have to consider this or remember to activate/deactivate the locking mechanism.

The reservoir may be a rigid cartridge comprising an axially moveable piston or it may be a flexible reservoir capable of undergoing controlled volume reduction. The injection means may comprise an axially moveable piston rod being adapted to act on the reservoir, either directly or via a coupling device, to reduce the volume of the reservoir, causing drug to be expelled therefrom. Mounting the cap on the cap receiving part may affect the injection means directly or indirectly by affecting an associated element. In any case, the cap, preferably the edge of the cap, affects the injection means mechanically in such a way that the injection means is incapable of being activated even if the user applies a very large force to the injection device.

The injection device may comprise a drive member adapted to slave the piston rod during forward axial movement in the injection device, i.e. during movement towards the distal end of the device. In that case when mounted on the cap receiving part the cap may physically block the drive member from axial forward movement, e.g. through abutting surfaces. The cap may, however, at the same time allow rotational movement of the drive member.

In a particular embodiment the injection device further comprises guiding means adapted to guide the movement of the drive member and/or the piston rod, and an injection button operatively coupled to the dose setting means and the injection means and axially moveable between a first position corresponding to a position in which the dose is set and a second position corresponding to a position in which the injection means has been activated to inject the set dose, wherein the injection button is able to perform substantially unimpeded movement from the first position to the second position and back to the first position when the cap is mounted on the injection device. In other words, the injection button can be manipulated, e.g. depressed, while the cap is mounted on the device. Such an arrangement allows for an injection device which is secured against premature activation of the injection mechanism, without incorporating a mechanical lock capable of withstanding large forces being applied to the injection button, e.g. as a result of the user playing with, mishandling or dropping the device.

If the guiding means comprises a first longitudinal guiding surface and a second sloping guiding surface, as described in connection with the second aspect of the invention, this may be implemented by arranging the drive member such that a part of the drive member abuts with the cap edge when the cap is mounted on the injection device. The cap thereby blocks the drive member from moving axially and the piston rod is thus also prevented from moving axially, in which case no dose can be ejected from the reservoir.

BRIEF DESCRIPTION OF THE DRAWINGS

The invention will now be described in further detail with reference to the accompanying drawings in which

FIG. 9 is a perspective view of the housing of the injection device, showing the position of the guiding means in the housing, FIG. 10a and FIG. 10b show the front side, respectively the back side of a piston rod of the injection device, FIG. 11 is a perspective view of a drive member of the injection device, FIG. 12 is a two-dimensional representation of the guiding means and the drive member, showing the drive member in two different positions with respect to the guiding means, FIG. 13 is a two-dimensional representation of guiding means further comprising a support shelf to enable initial priming, FIG. 24 is a perspective view of a drive member, FIG. 25 is a perspective view of a push button, FIG. 26 is a perspective view illustrating the functional connection between the push button and the drive member, FIG. 27 is a perspective view showing the engagement between the drive member and a piston rod, FIG. 28 is a perspective view showing an assembly of the piston rod, the drive member, the guiding means, and a spring, in a situation where the drive member rests on the dose shelves of the guiding means corresponding to a loaded condition of the injection device, FIG. 29 is a perspective view of an end-of-contents mechanism in the injection device.

In the figures like structures are mainly identified by like reference numerals.

DESCRIPTION OF EXEMPLARY EMBODIMENTS

Figure 1:
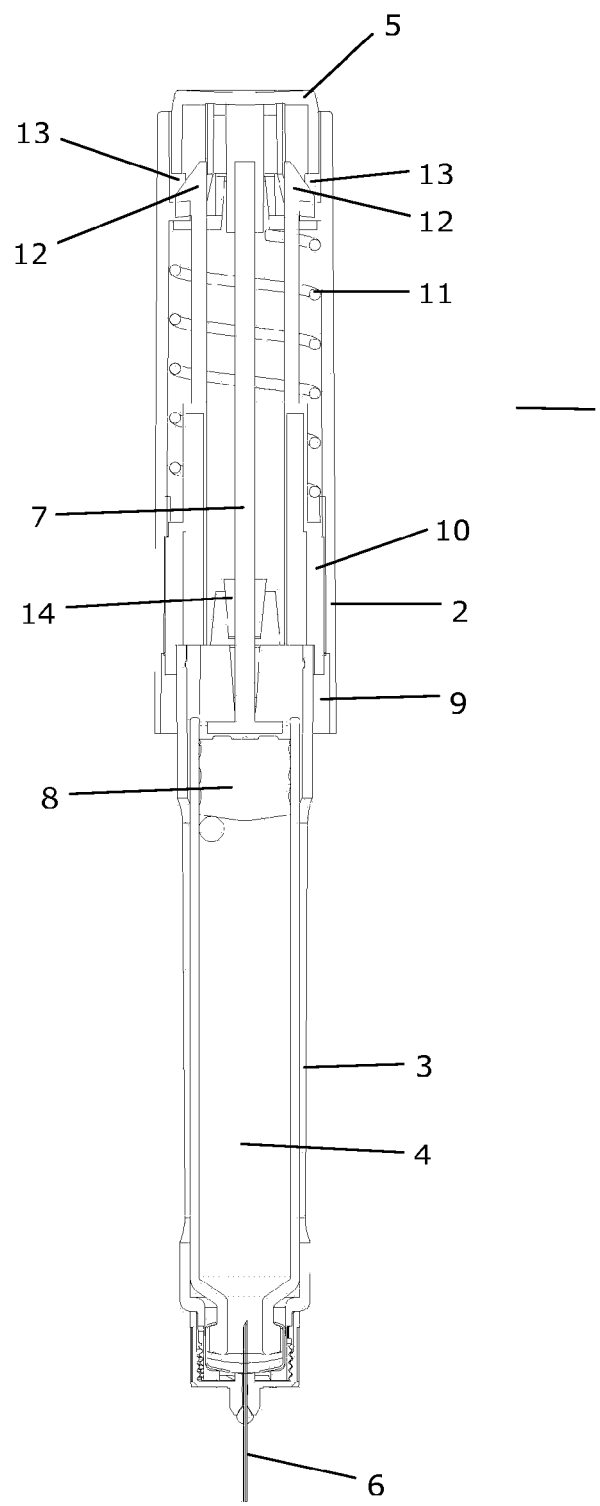
FIG. 1 is a cross sectional view of an injection device according to a first embodiment of the invention in an unloaded state.

FIG. 1 is a cross sectional view of an injection device 1 according to a first embodiment of the invention. In FIG. 1 the injection device 1 is shown in an unloaded state, i.e. a dose has not yet been set.

The injection device 1 comprises a housing 2, a cartridge holding part 3 having a cartridge 4 arranged therein, and an injection button 5. At a distal end of the cartridge holding part 3 an injection needle 6 is attached. A piston rod 7 is arranged in abutment with a piston 8 arranged in an interior part of the cartridge 3 in such a manner that moving the piston rod 7 in a distal direction will cause the piston 8 to move in a distal direction, thereby causing liquid drug from the cartridge 4 to be expelled via the injection needle 6.

When a user has completed an injection a cap (not shown in FIG. 1) is mounted on the injection device 1 at cap receiving part 9 in such a manner that the injection needle 6 is covered. When the cap is mounted at the cap receiving part 9 it pushes against slider 10, thereby moving it in a proximal direction. This causes spring 11 to be compressed, thereby storing energy in the spring 11, and moves snap arms 12 in a proximal direction to a position beyond protrusions 13 arranged on the housing 2. The protrusions 13 ensure that the snap arms 12 are retained in this position.

The slider 10 is connected to the piston rod 7 via teeth (not shown) formed on the piston rod 7 and a teeth engaging part 14 formed on the slider 10. The teeth and the teeth engaging part 14 are arranged in such a manner that the teeth engaging part 14 is allowed to pass over the teeth when the slider 10 is moved in a proximal direction relative to the piston rod 7, but the piston rod 7 must move along with the slider 10 when the slider 10 is moved in a reverse direction. Thus, moving the slider 10 in a proximal direction as described above causes the slider 10 to move relative to the piston rod 7, the moved distance corresponding to a predetermined dose, since the piston rod 7, and thereby the piston 8, will be moved along the same distance when the slider 10 is subsequently moved in a reverse direction.

Furthermore, the movement of the slider 10 in a proximal direction as described above causes the injection button 5 to be moved in a proximal direction, i.e. causing the injection button 5 to protrude from the housing 2, thereby indicating to a user that the injection device 1 has been loaded, i.e. a dose has been set.

Figure 2:
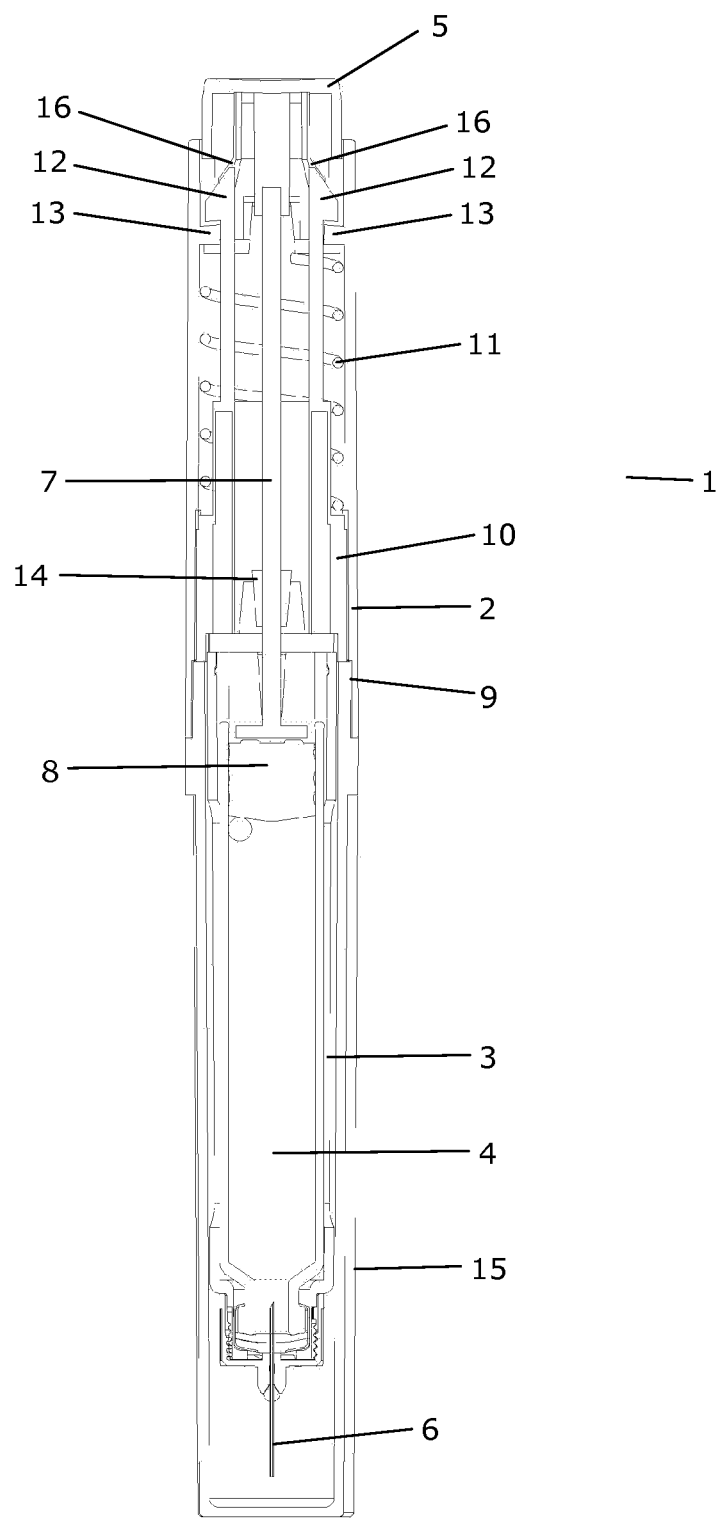
FIG. 2 is a cross sectional view of the injection device of FIG. 1 in a loaded state.

FIG. 2 is a cross sectional view of the injection device 1 of FIG. 1 in a loaded state. In FIG. 2 a cap 15 has been mounted on the injection device 1 at the cap receiving part 9. It is clear that the injection button 5 has been moved in a proximal direction as compared to the position shown in FIG. 1. It is also clear that the snap arms 12 have been moved in a proximal direction beyond the protrusions 13, and that the protrusions 13 retain the snap arms 12 in this position.

When it is desired to inject the set dose, the user removes the cap 15, thereby uncovering the injection needle 6, and inserts the injection needle 6 at a suitable injection site. The injection button 5 is then pushed in a distal direction, i.e. towards the housing 2 and the position shown in FIG. 1. This causes pushing surfaces 16 to push snap arms 12 towards the centre of the injection device 1, thereby releasing them from the protrusions 13. Accordingly, the slider 10 is allowed to move in a distal direction, and the energy stored in the spring 11 during setting of the dose will cause this movement to take place. Due to the engagement between the teeth of the piston rod 7 and the teeth engaging part 14 of the slider 10, the piston rod 7 is moved along. Thereby the piston 8 is also moved in a distal direction, thereby causing the predetermined dose to be expelled from the cartridge 4 via the injection needle 6.

When the injection has been completed, the cap 15 is once again mounted on the injection device 1 at the cap receiving part 9, thereby causing a new dose to be set as described above. It should be noted that since the slider 10 is moved the same distance each time the cap 15 is mounted on the injection device 1, the set dose is a predetermined, fixed dose.

Figure 3:
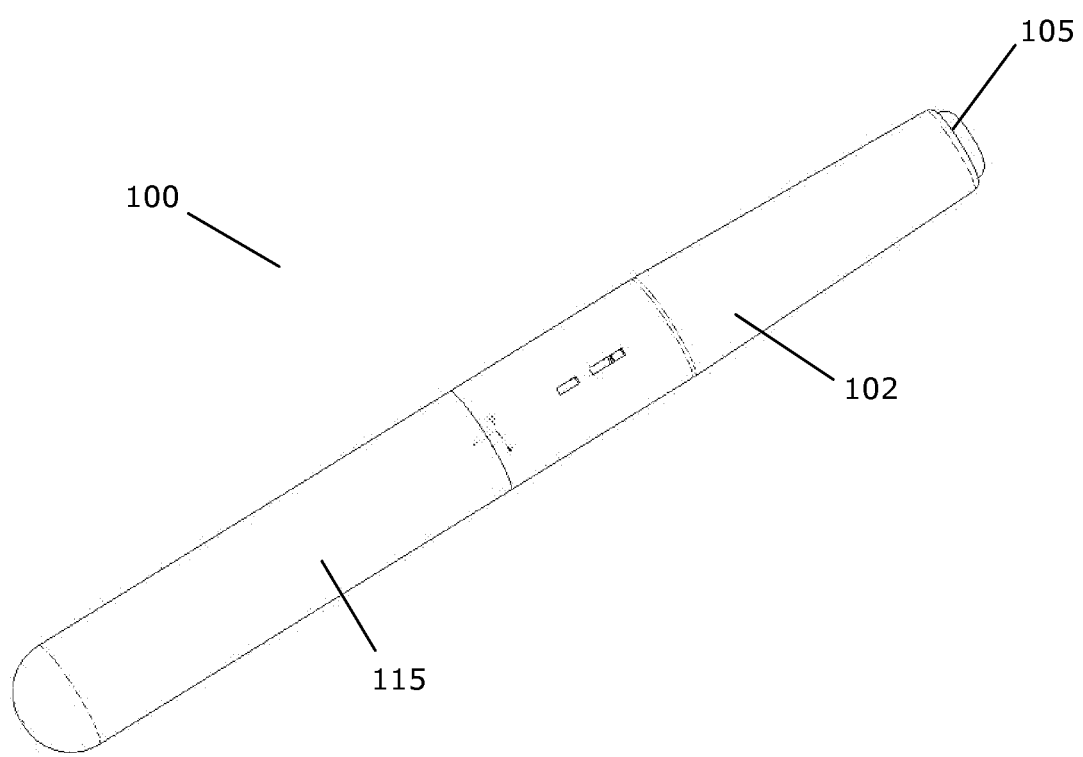
FIG. 3 is a perspective view of an injection device according to a second embodiment of the invention.

FIG. 3 is a perspective view of an injection device 100 according to a second embodiment of the invention. A housing 102 and an injection button 105 are visible, and a cap 115 is mounted on the injection device 100. Since the injection button 105 is positioned relatively close to the housing 102, it can be seen that the injection device 100 is not loaded, i.e. a dose has not been set.

Figure 4:
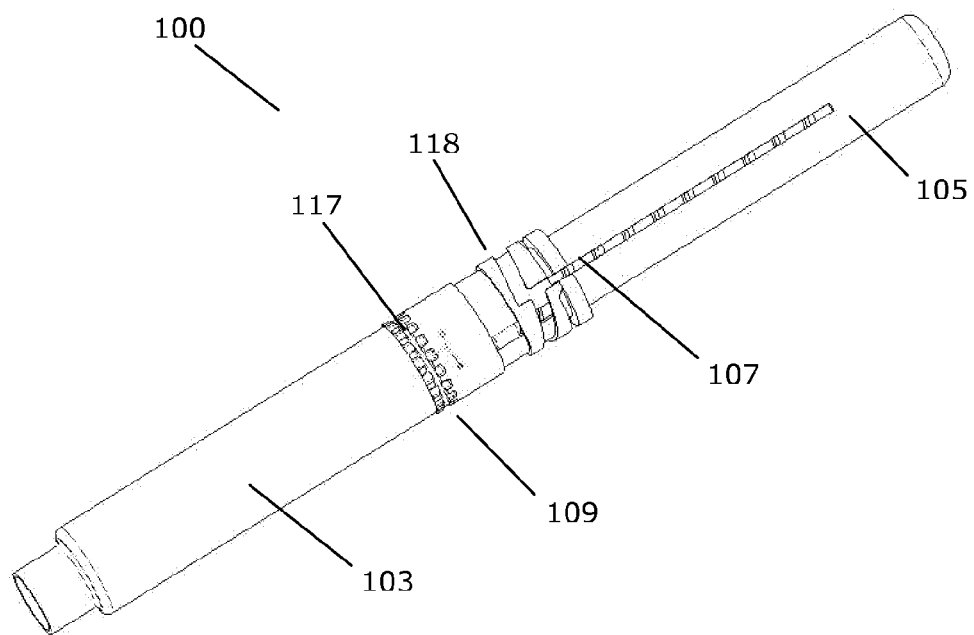
FIG. 4 is a perspective view of the injection device of FIG. 3 with some parts removed.

FIG. 4 is a perspective view of the injection device 100 of FIG. 3. For the sake of clarity, some of the parts, notably the cap and the housing, have been removed. This allows the cartridge holding part 103 and the injection button 105 to be seen. The injection device 100 of FIGS. 3 and 4 is preferably operated in the following manner. When it is desired to inject a dose, the cap 115 is removed from the injection device 100 by rotating the cap 115 relative to the housing 102, thereby uncovering an injection needle (not shown). The cap 115 engages the cartridge holding part 103 via teeth 117 arranged at the cap receiving part 109 in such a manner that when the cap 115 is rotated, the cartridge holding part 103 is rotated along. Rotating the cartridge holding part 103 in this manner causes track portion 118, which is actually a part of the cartridge holding part 103, to rotate. An inclined portion of the track of the track portion 118 engages a protrusion (not shown) formed on an inner part of the housing, and thereby the rotation of the track portion 118 causes the track portion 118 to be moved axially in a proximal direction relative to the housing.

Furthermore, rotating the cartridge holding part 103 causes the piston rod 107 to rotate. The injection button 105 is connected to a thread formed on the piston rod 107, and therefore rotation of the piston rod 107 results in a prolongation of the piston rod 107/injection button 105 assembly. As the piston rod 107 is not allowed to move in a distal direction, this prolongation causes the injection button 105 to move in a proximal direction, i.e. out of the housing. Thereby the injection device 100 is loaded.

Finally, the axial movement of the track portion 118 causes the cap 115 to be pushed away from the injection device 100.

After the cap 115 has been removed and the injection device 100 has been loaded as described above, the injection needle is inserted at a suitable injection site. The injection button 105 is then pushed in a distal direction, i.e. towards the housing 102. Due to axial locking between the injection button 105 and the piston rod 107 this movement results in axial movement of the piston rod 107, and thereby drug injection.

When the injection has been completed, the cap 115 is once again mounted on the injection device 100. This is done by pushing the cap 115 onto the injection device 100 in a substantially axial movement. Simultaneously, the injection button 105 must be pushed in a distal direction in order to properly fit the cap 115 onto the injection device 100.

Figure 5:
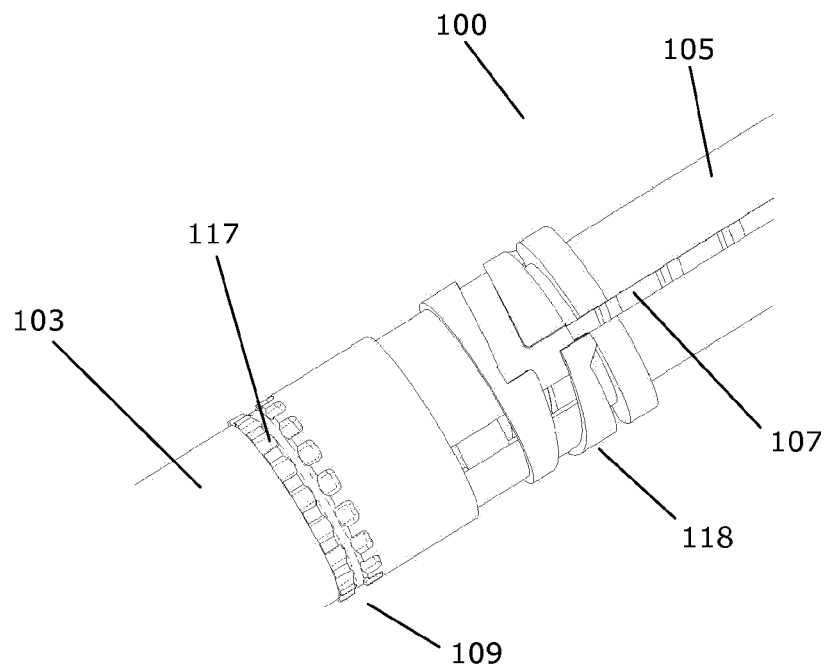
FIG. 5 is a detail of the injection device of FIGS. 3 and 4.

FIG. 5 is a detail of FIG. 4, in which the cap receiving part 109, the teeth 117 and the track portion 118 are seen more clearly.

Figure 6:
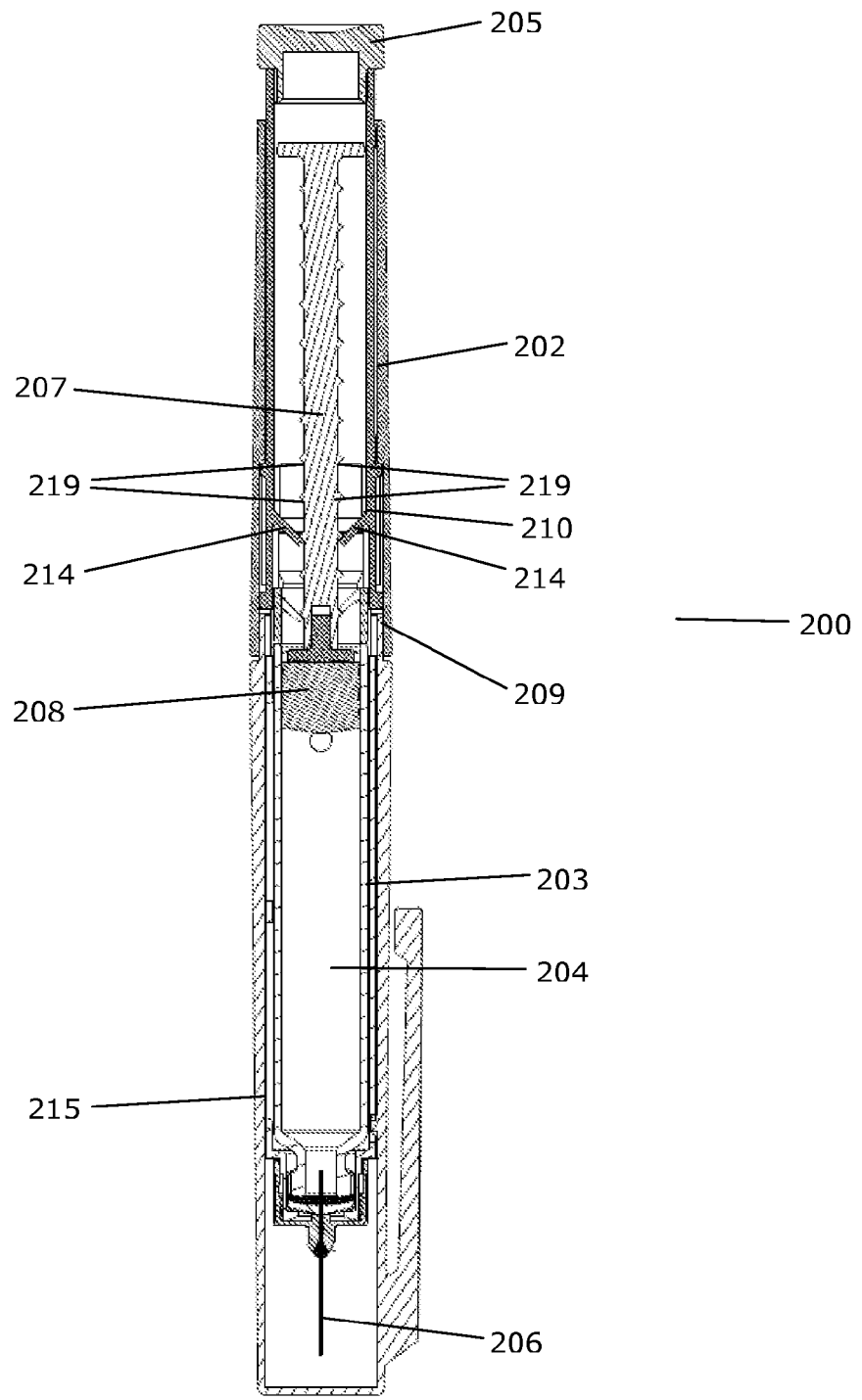
FIG. 6 is a cross sectional view of an injection device according to a third embodiment of the invention.

FIG. 6 is a cross sectional view of an injection device 200 according to a third embodiment of the invention. The injection device 200 is in a loaded state. The injection device 200 operates in a manner similar to the injection device 1 shown in FIGS. 1 and 2. However, in this case energy is not stored in a spring, and the user has to manually press the injection button 205 home in order to expel a set dose.

When an injection has been completed, the cap 215 is mounted on the injection device 200 at the cap receiving part 209. The cap 215 pushes against slider 210, thereby moving it in a proximal direction, the slider 210 thereby pushing the injection button 205 in a proximal direction, i.e. away from the housing 202 to the position shown in FIG. 6.

The slider 210 and the piston rod 207 are engaged via teeth 219 formed on the piston rod 207 and teeth engaging parts 214 formed on the slider 210. The teeth 219 and the teeth engaging parts 214 are arranged in such a manner that the teeth engaging parts 214 are allowed to pass over the teeth 219 when the slider 210 is moved in a proximal direction relative to the piston rod 207, and the piston rod 207 must be moved along when the slider 210 is moved in a reverse direction. Accordingly, moving the slider 210 in a proximal direction as described above, results in the slider 210 moving relative to the piston rod 207. The distance moved corresponds to a predetermined dose as described above.

When it is desired to inject the set dose, the user removes the cap 215, thereby uncovering the injection needle 206, and the injection needle 206 is inserted at a suitable injection site. The injection button 205 is then pushed in a distal direction, i.e. towards the housing 202.

This causes the slider 210 to move in a distal direction, and due to the engagement between the teeth 219 and the teeth engaging parts 214, the piston rod 207 is moved along. Thereby the piston 208 is also moved in a distal direction, and the set dose of drug is expelled via the injection needle 206.

Figure 7:
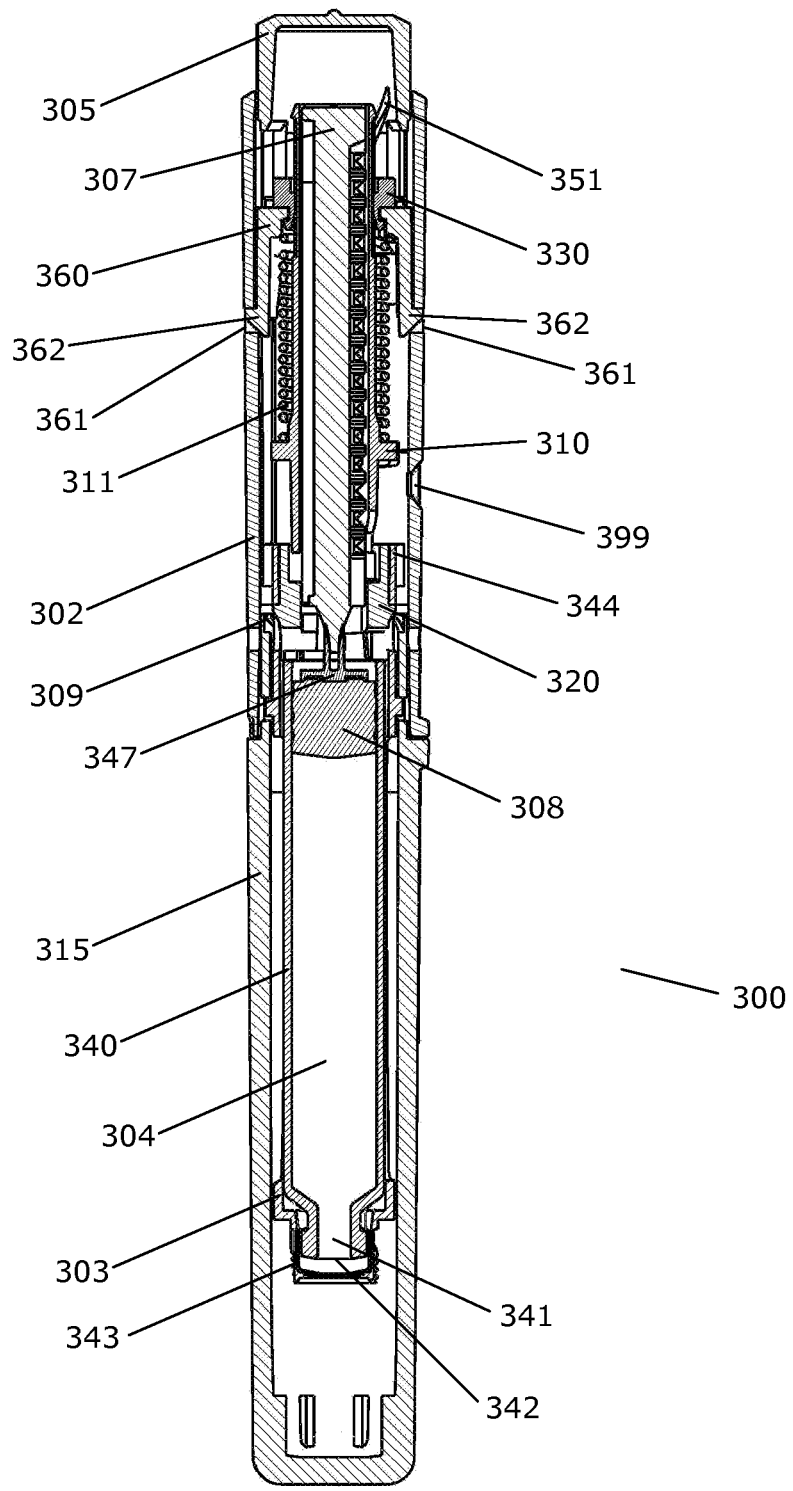
FIG. 7 is a cross sectional view of an injection device according to a fourth embodiment of the invention.

FIG. 7 is a cross sectional view of an injection device 300 according to a fourth embodiment of the invention. The injection device 300 generally comprises a housing 302 and a cartridge holding part 303 for supporting a cartridge 304 which contains the liquid drug. The liquid drug is positioned between a piston 308, which is capable of moving axially in the cartridge 304, a tubular cartridge wall 340, and a self-sealing septum 342 covering a drug outlet 341 through which the liquid drug is intended to flow when the piston is advanced in the cartridge 304 and when an injection needle (not shown) is attached to the drug outlet 341 via a needle hub interface 343. A cap 315 is mounted on a cap receiving part 309 in the housing 302, whereby it protects the cartridge 304 and covers the drug outlet 341. An injection button 305 being capable of reciprocating axial motion with respect to the housing 302 is shown in a position where it protrudes from the distal end of the housing 302. This indicates that the injection device 300 is in a loaded state, i.e. that a dose has been set and that the injection device 300 is ready to perform an injection (upon removal of the cap 315). This will be explained in greater detail below.

A piston rod 307 is attached to the piston 308 via a piston rod foot 347 and operatively coupled to the injection button 305 such that when the cap 315 is off, an injection needle has been attached to the needle hub interface 343, and the injection button 305 is pressed against the housing 302 the piston rod 307 will advance axially through the housing 302 a certain distance, thereby displacing the piston 308 in the cartridge 304 an equivalent distance to inject a desired amount of drug through the outlet 341.

The movement of the piston rod 307 is realised through a coupling ring 330 being in engagement with a helical track 351 in the injection button 305, and a driver 310 which is in engagement with the coupling ring 330 and which is adapted to engage with, and transmit a driving force to, the piston rod 307. The driver 310 is powered by a spring 311 which is a torsionally pre-tensioned compression spring capable of storing and releasing energy for both translational and rotational motion. One end of the spring 311 is retained in a spring base 360 and the other end of the spring 311 is in engagement with the driver 310 in such a way that the spring 311 and the driver 310 are able to interchange both forces and torques. The driver 310 is thus capable of performing both translational and rotational motion relative to the housing 302. The spring 311 may for example be torsionally pre-tensioned during assemblage of the injection device 300, e.g. by mutually twisting its two end parts a half or a full turn. When the cap 315 is dismounted from the injection device 300, the movement of the driver 310 is guided by a guide member 320.

The housing 302 has two radially opposite apertures 361, each adapted to receive a hook 362 provided on the spring base 360 to thereby retain the spring base 360 from translational as well as rotational movement relative to the housing 302. The housing 302 further has a window 399 useable for inspection of the current position of the driver 310 in the injection device 300.

Figure 8:
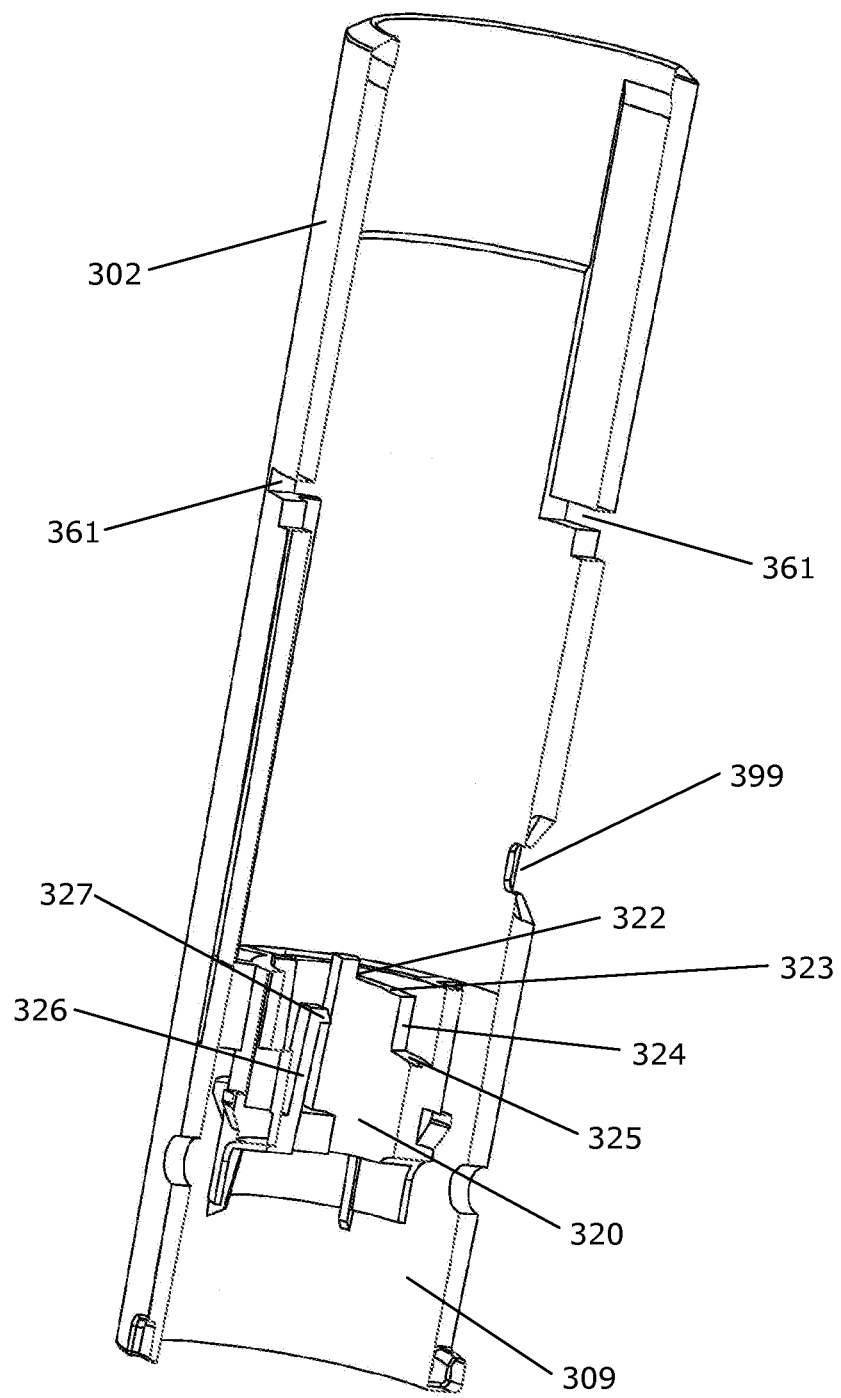
FIG. 8 is a cross sectional perspective view of the housing of the injection device, showing a guiding means in detail.

FIG. 8 is a cross sectional perspective view of the housing 302, which shows the guide member 320 in more detail. For the sake of clarity the proximal end 344 of the cartridge holding part 303 has been removed from the figure. The guide member 320 comprises a dose shelf 323 adapted to support and guide the driver 310 during the second part of the dose setting and the first part of the injection. A longitudinal guide surface 324 leads from the dose shelf 323 to an end of dose stop 325. The dose shelf 323 is a helical ramp segment which extends circumferentially from a connection with the longitudinal guide surface 324 to a longitudinal stop surface 322. A click finger 326 is provided on the guide member, the click finger 326 having a tip 327 for engagement with the piston rod 307.

FIG. 9 is a perspective view of the housing 302 as seen from the distal end. It shows the position of the guide member 320 within the housing 302. Again, for the sake of clarity the proximal end 344 of the cartridge holding part 303 has been removed from the figure. The guide member 320 is a generally tubular structure positioned concentrically with the housing 302 and connected to the housing 302 via a number of spacers 386. This connection to the housing 302 provides a tubular clearance 389 between the outer wall 329 of the guide member 320 and the inside of the housing 302. Some of this tubular clearance is, however, taken up by the tubular proximal end 344 of the cartridge holding part 303. The cap receiving part 309 comprises the remaining part of the tubular clearance 389 and a distal housing edge 385. A central bore 380 is provided allowing passage of the piston rod 307 through the guide member 320. The central bore 380 is adapted to guide axial movements of the piston rod 307.

FIG. 10a shows a first side of the piston rod 307. A number of teeth 319 are distributed along the piston rod 307, the distance between two consecutive teeth 319 being constant throughout the entire distribution. The teeth 319 are adapted for engagement with the driver 310 during dose injection where the driver 310 engages a tooth 319 and slaves the piston rod 307 in a forward motion. At its proximal end the piston rod 307 is provided with a stop face 393 adapted to restrict the movement of the driver 310 in an end-of-content situation.

FIG. 10b shows a second side of the piston rod 307. On this side a number of smaller teeth 396 are distributed, the distance between two consecutive teeth 396 equalling the distance between two consecutive teeth 319 on the first side of the piston rod 307. Between two consecutive teeth 396 a number of even smaller teeth 395 are distributed, the distance between two consecutive teeth 395 being constant throughout the distribution. The teeth 395 and 396 are intended to be overridden by tip 327 of click finger 326 during advancement of the piston rod 307 through the central bore 380. At its proximal end the piston rod 307 is provided with a longitudinal track 394 adapted to restrict the movement of the driver 310 in an end-of-content situation, preferably co-acting with stop face 393.

FIG. 11 is a perspective view of the drive member 310, generally comprising a tubular body 370 having two radially opposite longitudinal grooves 371 extending from its proximal end, and a pair of shoulders 377 connecting the tubular body 370 with a distal part which comprises various engagement elements. From the shoulders 377 project two legs 372 which are adapted to move in the tubular clearance 389. Each leg 372 has a foot section, the bottom of which constitutes a contact sole 374. The distal part of the driver 310 further comprises two slider elements 373 adapted to travel the guide surfaces of the guide member 320. One of the slider elements 373 is provided with a catch element 375. A tooth engaging element 376 is placed circumferentially between the two slider elements 373 and are rigidly connected to them such that the tooth engaging element 376 undergoes the same translational and/or rotational movement as the slider elements 373, and vice versa. During dose setting the tooth engaging element 376 is able to perform axial relative motion with respect to the piston rod 307, whereas during injection the tooth engaging element 376 is adapted to move into contact with a tooth 319 on the piston rod 307 and move the piston rod 307 axially a distance through the housing 302. The shoulders 377 act as a bearing face for the spring 311 and are thereby the physical interface for the exchange of axial forces between the spring 311 and the driver 310. Adjacent one of the shoulders 377 is an abutting surface 378 adapted to abut with the distal end of the spring 311 for the exchange of torques between the spring 311 and the driver 310.

FIG. 12 is a two-dimensional representation of the guide member 320 and the driver 310, showing one of the slider elements 373 in two different positions on the guide member 320. It is understood that the guide member 320 comprises two sets of guiding surfaces which the two slider elements 373 travel simultaneously. However, as this movement of the slider elements 373 along the respective guiding surfaces is identical only one of them is presented. The dose shelf 323 and the longitudinal guide surface 324 are mutually connected at an angle θ. The connection point between the dose shelf 323 and the longitudinal guide surface 324 can be termed a ramp edge 328 and it constitutes a transition point between sliding motion of the slider element 373 along the longitudinal guide surface 324 and sliding motion of the slider element 373 along the sloping dose shelf 323. The spiralling motion of the slider element 373 along the dose shelf 323 is limited by the stop surface 322 and the axial motion of the slider element 373 along the longitudinal guide surface 324 is limited by the end of dose stop 325. The axial length of the longitudinal guide surface 324 is H, i.e. when the slider element 373 is positioned exactly at the ramp edge 328 it is lifted a distance H from the end of dose stop 325. Due to the slope of the dose shelf 323 in addition to a rotational movement the slider element 373 also performs an axial movement, D, when it travels the dose shelf 323 from the ramp edge 328 to the stop surface 322. When the slider element 373 is positioned at the stop surface 322 it is thus lifted an axial distance equalling H+D from the end of dose stop 325. The axial dimension H+D is notably larger than the distance between two consecutive teeth 319 on the piston rod 307, which is again larger than, or equal to, the axial dimension H.

Due to the torsionally pre-tensioned spring 311, the slider element 373 is biased against the stop surface 322 when it is positioned on the dose shelf 323 and against the longitudinal guide surface 324 when it is positioned at the end of dose stop 325 (it is in fact biased against the longitudinal guide surface 324 at any position below the ramp edge 328). The spring 311 is also axially pre-tensioned biasing the slider element 373 towards the end of dose stop 325. The characteristics of the spring 311 and the slope of the dose shelf 323 are, however, dimensioned such that when the slider element 373 is positioned above the ramp edge 328 the torque provided by the spring 311 is able to overcome the axial force of the spring 311 and the slider element 373 will be forced towards the stop surface 322.

FIG. 13 is a two-dimensional representation of the guide member 320 and the driver 310 in a variant where the guide member 320 further comprises a support shelf 321 for supporting the slider element 373 prior to the first use of the injection device 300. Due to the biasing torque of the spring 311 the slider element 373 is secured on the support shelf 321 until the device is taken into use. The slider element 373 is capable of sliding along the support shelf 321 and the stop surface 322 to take up a position on the dose shelf 323 in a manner similar to its movement from the dose shelf 323 to the end of dose stop 325. The slider element 373 is, however, not able to move from the dose shelf 323 back to the support shelf 321, i.e. once the slider element 373 has been transferred away from the support shelf 321, it can only move between the dose shelf 323 and the end of dose stop 325. The axial length of the stop surface 322 is P, i.e. the slider element 373 travels the axial distance P when moved from the support shelf 321 to the dose shelf 323. Since P is, relatively, much smaller than H, and there may further be a small axial clearance between the piston rod 307 and the piston 308 when the injection device 300 is supplied by the manufacturer, when the injection device 300 is used for the first time the piston rod 307 will perform a much smaller axial movement than during subsequent uses, thereby enabling an initial priming that does not waste an approximately full dose of the liquid drug.

Figure 14:
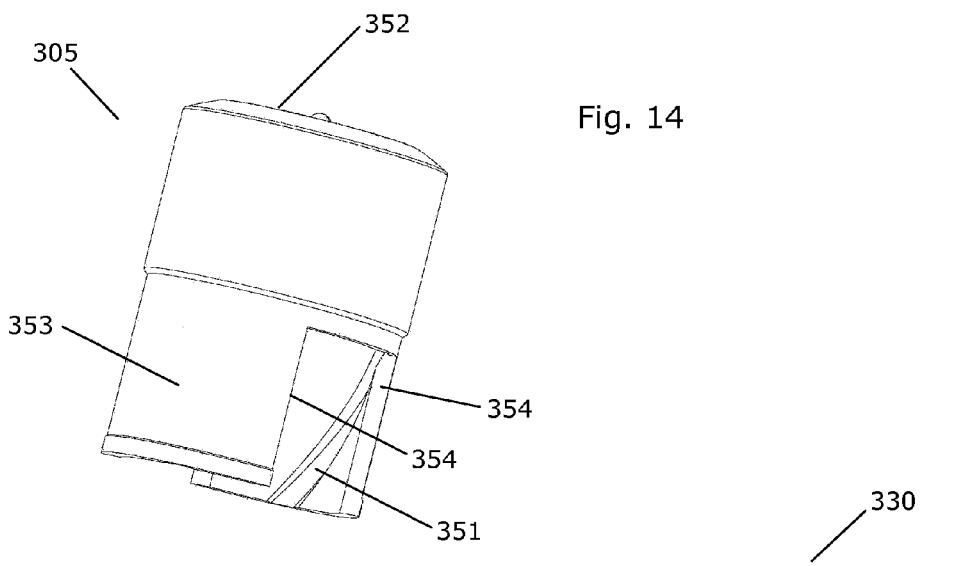
FIG. 14 is a perspective view of a push button of the injection device.

FIG. 14 is a perspective view of the injection button 305 comprising a push face 352 for interfacing with an operator of the injection device 300. The injection button 305 further comprises two flanges 353, each provided with a helical track 351 and two flange sides 354.

Figure 15:
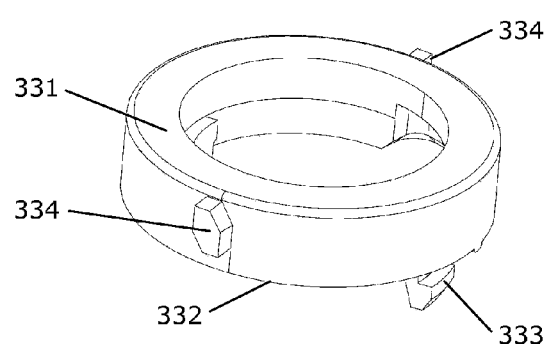
FIG. 15 is a perspective view of a coupling element of the injection device.

FIG. 15 is a perspective view of the coupling ring 330 adapted to couple the injection button 305 and the driver 310. The coupling ring 330 has a proximal face 331 and a distal face 332 and two radially opposite tongues 333 adapted to engage with the grooves 371 in the tubular body 370 of the driver 310 to rotationally lock the coupling ring 330 to the driver 310. The tongues 333 are further adapted to engage with the spring base 360 to translationally lock the coupling ring 330 to the spring base 360. The coupling ring 330 and the driver 310 are able to perform relative translatory motion limited by the length of the grooves 371. Two protrusions 334 are provided to engage with, and travel, the helical tracks 351 in the flanges 353 to thereby transform rotational motion of the coupling ring 330 to translational motion of the injection button 305, and vice versa.

Figure 16:
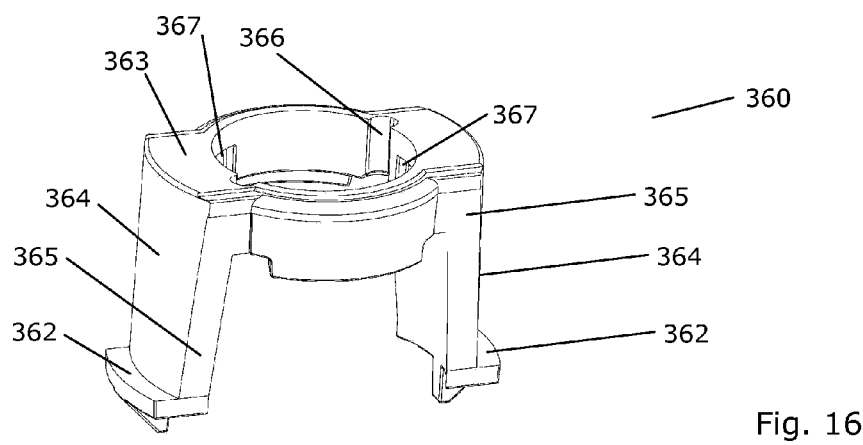
FIG. 16 is a perspective view of a spring retaining means of the injection device.

FIG. 16 is a perspective view of the spring base 360 which is adapted to hold one end of the spring 311 in a permanent position with respect to the housing 302. The spring base 360 has two radially opposite arms 364 each comprising a hook 362 for engagement with the respective apertures 361 in the housing 302, and two contact faces 365 adapted to abut with the flange sides 354, thereby preventing the injection button 305 from rotating relative to the spring base 360. Due to the engagement between the hooks 362 and the apertures 361 the spring base 360 is completely locked to the housing 302, i.e. the spring base 360 is prevented from performing rotational as well as translatory motion relative to the housing 302. A spring retaining groove 366 is provided for retaining the proximal end of the spring 311. The spring base 360 further comprises a proximal face 363 adapted to abut with the distal face 332 of the coupling ring 330, and two circumferential grooves 367 adapted to slidably engage with the tongues 333 and to retain the tongues 333 with respect to axial movement. The coupling ring 330 is thereby translationally locked to the spring base 360, but capable of rotating relative thereto, the rotational motion being limited by the circumferential dimension of the grooves 367.

Figure 17:
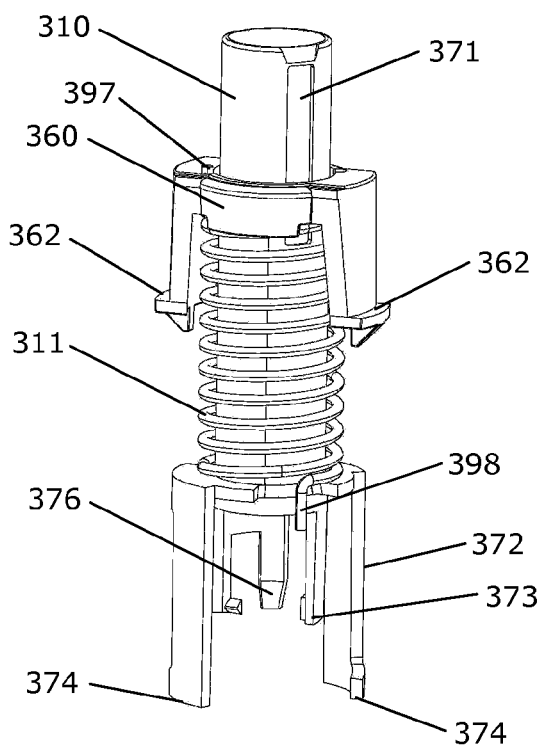
FIG. 17 is a perspective view showing an assembly of the drive member, a spring, and spring retaining means.

FIG. 17 is a perspective view showing an assembly of the driver 310, the spring 311, and the spring base 360. The proximal spring end 397 is retained in the spring base 360 and the distal spring end 398 is in connection with the driver 310. As the spring base 360 is locked to the housing 302 and thereby unable to move the torsionally pre-tensioned spring 311 will bias the driver 310 anti-clockwise, as seen from the spring base 360.

Figure 18:
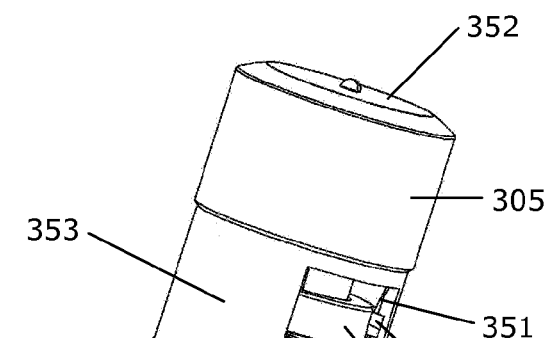
FIG. 18 is a perspective view illustrating the functional connection between the push button and the drive member.
Figure 18:
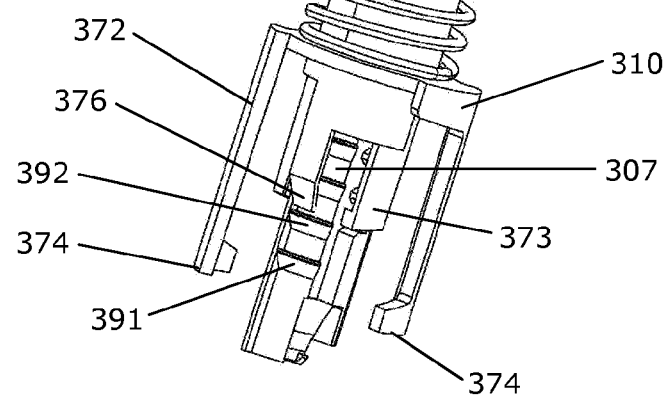

FIG. 18 is a perspective view illustrating the functional connection between the injection button 305 and the driver 310. A push on the push face 352 will force the injection button 305 downwards towards the spring base 360. As the injection button 305 is locked against rotation relative to the spring base 360 this downwards movement is purely translational. During the translational movement of the injection button 305 the protrusions 334 travel the helical tracks 351. This engagement converts the movement of the injection button 305 to a rotational movement of the coupling ring 330, and since the coupling ring 330 is rotationally locked to the driver 310, also the driver 310 will rotate. The helical tracks 351 are arranged such that when the injection button 305 is pushed towards the spring base 360 the coupling ring 330, and thereby the driver 310, will rotate clockwise, as seen from the spring base 360, i.e. against the rotational bias of the spring 311.

Figure 19:
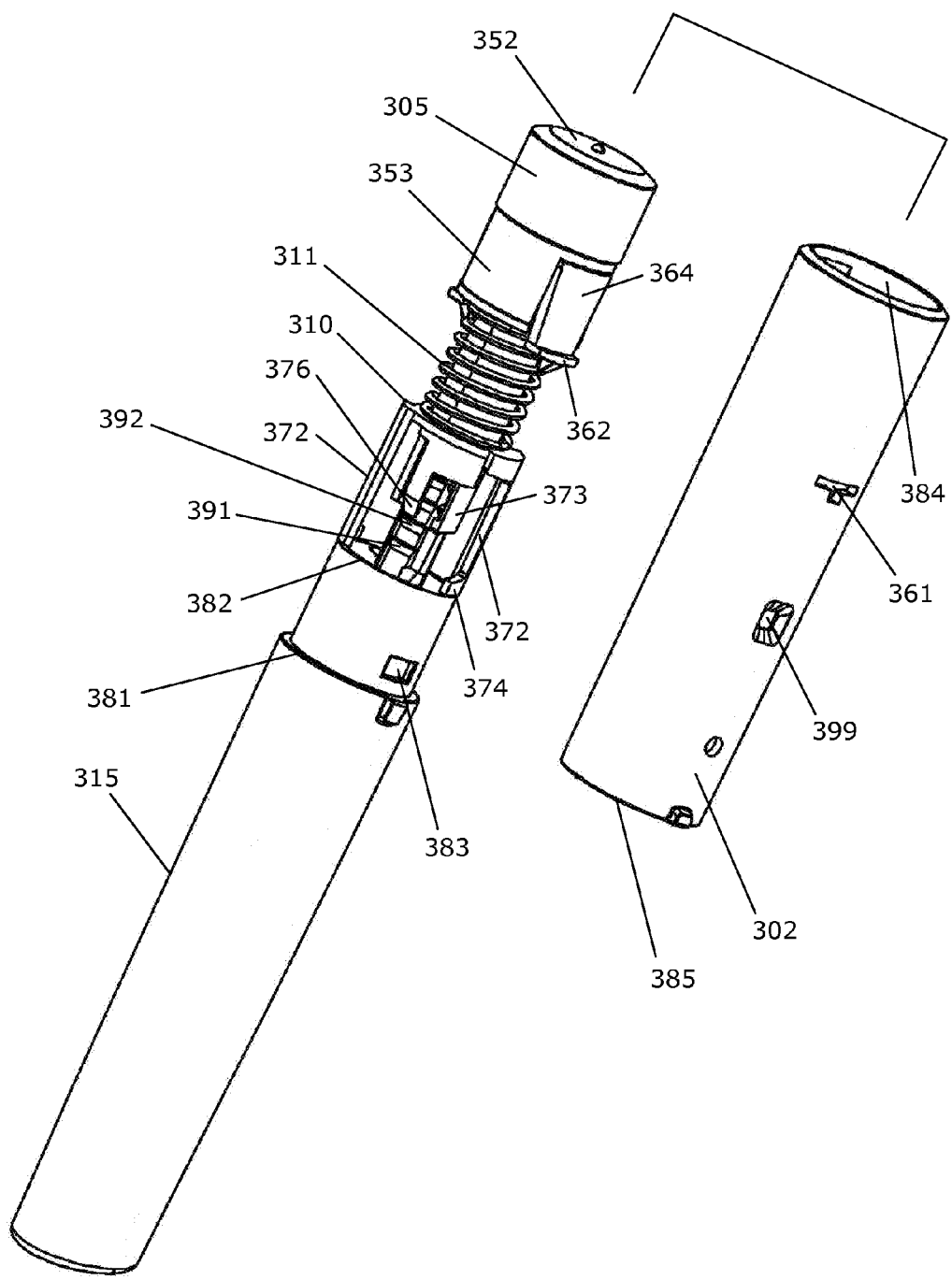
FIG. 19 is a perspective view of the injection device with the housing removed, showing an interaction between the drive member and the protective cap.

FIG. 19 is a perspective view of the injection device 300 with the housing 302 removed, showing an interaction between the driver 310 and the cap 315 when the cap 315 is mounted on the injection device 300 to cover and protect the distal part of the injection device 300. For the sake of clarity the proximal end 344 of the cartridge holding part 303 has been removed from the figure. When the cap 315 is completely received in the cap receiving part 309 an annular abutting surface 381 on the cap 315 abuts the distal housing edge 385, and a cap edge 382 abuts the contact soles 374 of the driver 310. This corresponds to a situation where the injection device 300 is loaded, i.e. a dose has been set. As long as the injection device 300 still contains enough liquid drug to provide a full dose the injection button 305 will in such a situation protrude from a proximal housing opening 384. In FIG. 19, however, the injection button 305 is depressed against the spring base 360. This illustrates a situation where a user has tried to activate the injection mechanism to eject the set dose from the cartridge 304 when the cap 315 is mounted on the injection device 300. In such a case depressing the injection button 305 will still cause a rotation of the driver 310 against the biasing torque of the spring 311, but since the cap edge 382 blocks against translational movement of the driver 310 via the interface with the contact soles 374 the contact soles 374 will just slide along the cap edge 382 and no ejection will take place. When the user removes the push force from the injection button 305 the biasing torque of the spring 311 will force the driver 310 to rotate in the opposite direction until the slider elements 373 meet the respective stop surfaces 322 (not visible). During this movement the contact soles 374 will slide along the cap edge 382 back to their original positions on the cap edge 382, and the injection button 305 will be forced to project out of the proximal housing opening 384 due to the threaded engagement with the coupling ring 330. Apertures 383 in the cap 315 are adapted to receive respective beads (not shown) on the cartridge holding part 303 to ensure that the cap 315 is able to withstand a certain push force from the contact soles 374 due to the translational bias of the spring 311 when the driver 310 is rotated to a position corresponding to the slider elements' 373 passage of the ramp edges 328 (not visible).

Figure 20:
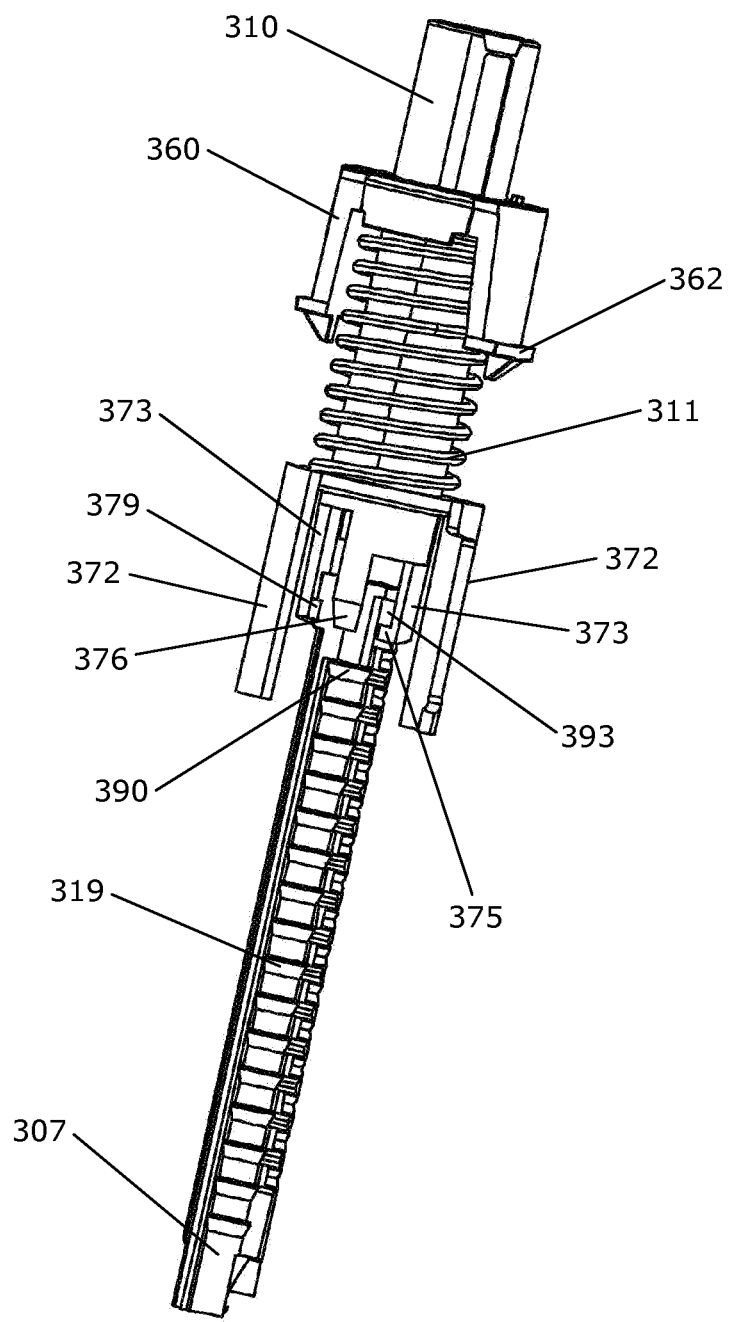
FIG. 20 is a perspective view of an end-of-contents mechanism in the injection device.

FIG. 20 is a perspective view of an end-of-content mechanism in the injection device 300. In FIG. 20 the tooth engaging element 376 has passed the most proximal positioned tooth 390 on the piston rod 307 and slaved the piston rod 307 to cause an injection of the last remaining full dose in the cartridge 304, and the driver 310 has responded to a remounting of the cap 315 by moving proximally with respect to the piston rod 307. As long as more doses remain in the cartridge 304 repositioning the cap 315 in the cap receiving part 309 will lead to both a translatory and a rotational movement of the driver 310, as will be explained in greater detail below. However, when the last full dose has been injected repositioning the cap 315 in the cap receiving part 309 will only lead to a translatory movement of the driver 310 due to the construction of the proximal end of the piston rod 307 and the distal part of the respective slider elements 373. The stop face 393 at the proximal end of the piston rod 307 is adapted to abut with the catch element 375 to prevent anti-clockwise rotation of the driver 310 with respect to the piston rod 307. Further, the longitudinal track 394 (not visible) is adapted to receive a protrusion 379 to thereby prevent the driver 310 from rotating with respect to the piston rod 307. The protrusion 379 is received in the longitudinal track 394 at the same time as the catch element 375 engages with the stop face 393, and the stop face 393 and the longitudinal track 394 thus reinforce each others individual restriction of the freedom of movement of the driver 310.

Operation of the Infection Device Represented by FIGS. 7-20

In the following a situation of use of the injection device according to the fourth embodiment of the invention, as depicted in FIGS. 7-20, will be described. The injection device 300 shown in FIG. 7 is in a non-use state having the cap 315 mounted thereon. When the user needs to perform an injection he/she removes the cap 315 from the injection device 300 and attaches an injection needle to the needle hub interface 343. The injection device 300 is already loaded and ready to inject the set dose so the user simply selects the injection site, positions the injection needle in the skin and pushes the injection button 305 which protrudes from the housing opening 384 at the proximal end of the housing 302. Pushing the injection button 305 in the distal direction towards the housing 302 causes a substantially pure translatory displacement of the injection button 305 relative to the housing 302 due to the contact faces 365 preventing rotation of the injection button 305 via the engagement with the flange sides 354. This translatory displacement of the injection button 305 causes the protrusions 334 to travel the helical tracks 351. Since the coupling ring 330 is axially locked with respect to the housing 302, due to the engagement between the tongues 333 and the circumferential grooves 367 in the spring base 360 being completely locked with respect to the housing 302, when the protrusions 334 travel the helical tracks 351 the translatory movement of the injection button 305 is transformed into a rotational movement of the coupling ring 330 relative to the housing 302. The engagement between the tongues 333 and the longitudinal grooves 371 in the tubular body 370 forces the driver 310 to rotate along with the coupling ring 330.

The rotation of the driver 310 caused by the depression of the injection button 305 is performed against the biasing torque of the spring 311. In the situation where the user has not yet depressed the injection button 305 the slider elements 373 rests on the respective dose shelves 323 being biased against the stop surfaces 322 by the spring torque. Depressing the injection button 305, and thereby causing a rotation of the driver 310, will lead to the slider elements 373 being slid down the dose shelves 323 towards the ramp edges 328. When the injection button 305 is substantially fully depressed in the housing 302 the slider elements 373 reach the transition point at the ramp edges 328 at which point the spring 311 will release its stored translational energy and force the slider elements 373, via the abutment with the shoulders 377 on the driver 310, down along the longitudinal guide surfaces 324 towards the end of dose stop 325. During the movement of the slider elements 373 along the longitudinal guide surfaces 324 the tooth engaging element 376, being in engagement with a tooth 319 of the piston rod 307, will move along and thereby force the piston rod 307 to perform a corresponding axial forward movement through the central bore 380. Since the piston rod 307 is connected to the piston 308 such a forward movement of the piston rod 307 will cause a corresponding advancement of the piston 308 in the cartridge 304, leading to the ejection of the set dose from the cartridge 304. Hence, following a substantially full depression of the injection button 305, the spring 311 will automatically eject the liquid drug from the injection device 300 whether or not the user keeps a pressure on the push face 352. While the piston rod 307 moves axially to expel the set dose the tip 327 of the click finger 326 rides over the teeth 395 of the piston rod 307 being distributed between two consecutive larger teeth 396, thereby providing an audible feedback mechanism indicating to the user through audible clicks that the dosage is progressing. Just as the piston rod 307 stops its forward movement when the slider elements 373 are at the end of dose stop 325 the tip 327 rides over a larger tooth 396 providing a distinguishable audible indication, such as a larger click sound, of the fact that the movement of the piston 308 has stopped and that the dosage in principle is completed. When the slider elements 373 are at the end of dose stop 325 the driver 310 will be positioned such in the housing 302 that it completely covers the window 399, thereby also providing a visual end of dose indication. The user may then wait a few seconds before taking the injection needle out of the skin. However, when this happens, all the user has to do to prepare the injection device 300 for the next injection is to reposition the cap 315 in the cap receiving part 309, i.e. to put the cap 315 back on the injection device 300.

Repositioning the cap 315 in the cap receiving part 309 after an injection will cause a next dose to be set, as explained in the following. Due to the threaded engagement between the injection button 305 and the coupling ring 330 the injection button 305 will stay depressed in the housing 302 when the user releases the pressure from the push face 352 following the activation of the injection mechanism. This indicates to the user that the injection mechanism has been activated and that a dose is either being expelled or has been expelled from the cartridge 304. When the cap 315 is repositioned in the cap receiving part 309 after an injection the cap edge 382 will abut the contact soles 374 on the legs 372 of the driver 310. As the cap edge 382 during this repositioning of the cap 315 is moved gradually further towards the proximal end of the injection device 300 (when the annular abutting surface 381 moves towards abutment with the distal housing edge 385) it will push the driver 310 in the proximal direction accordingly. The driver 310 is thereby displaced axially against the translational biasing force of the spring 311 as the slider elements 373 move up along the longitudinal guide surfaces 324 towards the ramp edges 328. When the driver 310 is moved so far proximally by the cap edge 382 that the slider elements 373 reach the ramp edges 328 the torsional tension of the spring 311, having actually been increased during the injection procedure, will move the slider elements 373 up along the dose shelves 323 to the stop surfaces 322, thereby rotating the driver 310 relative to both the piston rod 307 and the housing 302. Since the dose shelves 323 are sloped this movement of the slider elements 373 will also cause the driver 310 to perform a small additional axial movement. The movement of the driver 310 causes the tooth engaging element 376 to perform an identical combined translatory and rotational movement, whereby it is lifted out of engagement with one tooth 391 on the piston rod 307 to pass the next more proximally positioned tooth 392. Since the axial displacement of the driver 310 during movement of the slider elements 373 from the end of dose stop 325 to the stop surfaces 322, H+D, is larger than the distance between two consecutive teeth 319 on the piston rod 307 the tooth engaging element 376 actually passes the next tooth 392 and leaves a small space between them, as shown in FIG. 18. As long as the cap 315 is positioned in the cap receiving part 309 in such a way that the cap edge 382 has not yet moved the driver 310 proximally to a point where the slider elements 373 have passed the ramp edges 328, the tooth engaging element 376 has not passed the next tooth 392, and if the cap 315 in such a situation is removed from the injection device 300 the translational bias of the spring 311 will move the slider elements 373 back to the end of dose stop 325, whereby the driver 310 will return to the position it takes following an injection and the tooth engaging element 376 will move back into engagement with the tooth 391. In other words the injection mechanism is not activated. However, if the cap 315 is positioned in the cap receiving part 309 such that the cap edge 382 moves the driver 310 proximally to an extent where the slider elements 373 pass the transition point at the ramp edges 328 the spring 311 will release its stored rotational energy and move the slider elements 373 along the dose shelves 323 to a position at the stop surfaces 322. This rotational movement is performed against the translational bias of the spring 311 which means that the slope of the dose shelves 323 must be within certain limits to enable the angular displacement of the driver 310. In this case, the slope of the dose shelves is approximately 10°, i.e. the angle θ is approximately 260°.

When the driver 310 is rotated due to the slider elements 373 travelling the dose shelves 323 the tooth engaging element 376 is moved from a position just below the next tooth 392 (corresponding to the position of the slider elements 373 just below the ramp edges 328) to a position above the tooth 392 in a combined translatory and rotational motion. This combined translatory and rotational motion is caused by the spring 311 releasing its stored rotational energy when the slider elements 373 pass the ramp edges 328, i.e. when this transition point is reached the user is no longer in control of the dose setting and the dose will be set no matter if the user dismounts the cap 315 from the injection device 300 or tries other manoeuvres to stop it. Furthermore, the torsional pre-tensioning of the spring 311 assures a stabile position of the slider elements 373 on the dose shelves 323 at the stop surfaces 322, whereby the injection device 300 is also secured from being fired until the user activates the injection mechanism to inject the set dose.

Since the driver 310 and the coupling ring 330 are rotationally locked the rotation of the driver 310 in connection with the dose being set causes the coupling ring 330 to rotate along, whereby the protrusions 334 will travel the helical tracks 351 in the injection button 305 and cause the injection button 305 to translate out of the proximal housing opening 384. As the driver 310 only rotates when the slider elements 373 have passed the ramp edges 328 and a dose is actually being set, the injection button 305 will only protrude from the housing 302 when a dose is set. This gives a clear signal to the user that either no dose is set or a dose is set and the injection device is ready for injection. In other words, when the cap 315 is mounted properly on the injection device 300 a dose is automatically set by the injection device 300 and the injection button 305 is automatically moved out of the housing 302 to indicate that the device is ready for use.

When the cap 315 is mounted on the injection device 300 it is not possible to activate the injection mechanism to eject a dose out of the reservoir 304. This will be explained in the following. As mentioned above, when positioning the cap 315 in the cap receiving part 309 the cap edge 382 will abut the contact soles 374 and move the driver 310 proximally in the housing 302. This action will move the driver 310 away from the window 399, and when the slider elements 373 are secured on the dose shelves 323 and a dose is set, the user can not see the driver 310 through the window 399. As long as the cap 315 is mounted on the injection device 300 the cap edge 382 abuts the contact soles 374. If the user tries to activate the injection mechanism by pressing the injection button 305 towards the housing 302, he/she will be unsuccessful because the cap edge 382 prevents any advancement of the piston rod 307 through the housing 302. The injection button 305 is free to move towards the housing 302. As the injection button 305 moves towards a depressed state the coupling ring 330 will rotate and this will cause the driver 310 to rotate against the rotational bias of the spring 311, as explained above in connection with an injection procedure. However, instead of moving down the sloping dose shelves 323 the slider elements 373 will just rotate while maintaining the same axial position. This is due to the contact soles 374 sliding along the cap edge 382 and not being able to perform an axial movement. When the injection button 305 is fully depressed in the housing 302 the driver 310 has been subjected to an angular displacement corresponding to a displacement of the slider elements 373 from the position on the dose shelves 323 at the stop surfaces 322 to a position past the ramp edges 328, at a height H+D above the end of dose stop 325. If the user releases the pressure from the injection button 305 the torsionally pre-tensioned spring 311 will immediately force the driver 310 to perform a reverse rotation. This is possible since the slider elements 373 are positioned above the ramp edges 328, and when the driver 310 rotates so does the coupling ring 330. The reverse rotation of the coupling ring 330 then causes the injection button 305 to travel out of the housing opening 384 and back to its most proximal position indicating that a dose is set and the injection device 300 is ready for injection. In other words, the user is able to press the injection button 305 against the housing 302 when the cap 315 is mounted on the injection device 300 without this leading to any drug being expelled from the reservoir 304. And when the user releases the pressure from the injection button 305, the injection device 300 will automatically push the injection button 305 back out of the housing 302 due to the spring 311 releasing stored energy for rotational reverse motion of the driver 310. When the slider elements 373 are at the position above the end of dose stop 325, i.e. on the other side of the ramp edges 328, the translational bias of the spring 311 will try to force the driver 310 axially in the distal direction against the contact force from the cap edge 382. The spring 311 is however not capable of moving the cap 315 out of the cap receiving part 309 due to the engagement between the cap 315 and the cap receiving part 309. Furthermore, beads (not shown) on the cartridge holding part 303 engage with the apertures 383 in the cap 315 to reinforce the connection. An injection device is thereby provided which is incapable of ejecting drug out of the reservoir when capped, while at the same time allowing the injection button to move freely in and out of the housing.

When the injection device 300 has been used for injection a number of times and the last full dose has just been ejected out of the cartridge 304 the tooth engaging element 376 is in engagement with the most proximal tooth 390 on the piston rod 307. If the user puts the cap 315 back on the injection device 300 the cap edge 382 will, as before explained, move the driver 310 proximally in the housing 302 whereby the tooth engaging element 376 will be lifted out of engagement with the tooth 390. However, as the slider elements 373 approach the transition point at the ramp edges 328, the catch element 375 engages with the stop face 393 and the protrusion 379 slides into the longitudinal track 394. The driver 310 is thereby prevented from rotating with respect to the piston rod 307. Since the piston rod 307 is rotationally locked in the central bore 380 it is not able to rotate with respect to the housing 302. The driver 310 is therefore in this particular situation not able to rotate relative to the housing 302. As the driver 310 and the coupling ring 330 are rotationally locked the coupling ring 330 will also not rotate and the injection button 305 is thus not moved out of the housing opening 384. This is a clear signal to the user that the last dose has been injected and the injection device 300 is empty.

It is clear from the above description that the transition point at the ramp edges 328 constitutes a boundary between manual and automatic actions in the respect that during dose setting all that happens before the slider elements 373 reach the ramp edges 328 is in the hands of the user, whereas when the slider elements 373 pass the ramp edges 328 the injection device 300 will take over and automatically set the dose and secure the injection mechanism, while during injection all that happens as long as the slider elements 373 are positioned on the dose shelves 328 is in the hands of the user, whereas when the slider elements 373 pass the ramp edges 328 the injection device 300 will perform an automatic injection which can not be aborted.

FIGS. 21-30 show an injection device 400 according to a fifth embodiment of the invention. The injection device 400 is operationally identical to the injection device 300 and it generally includes the same features as that device. However, there are certain structural differences between the two which will be clear from the below description.

Figure 21:
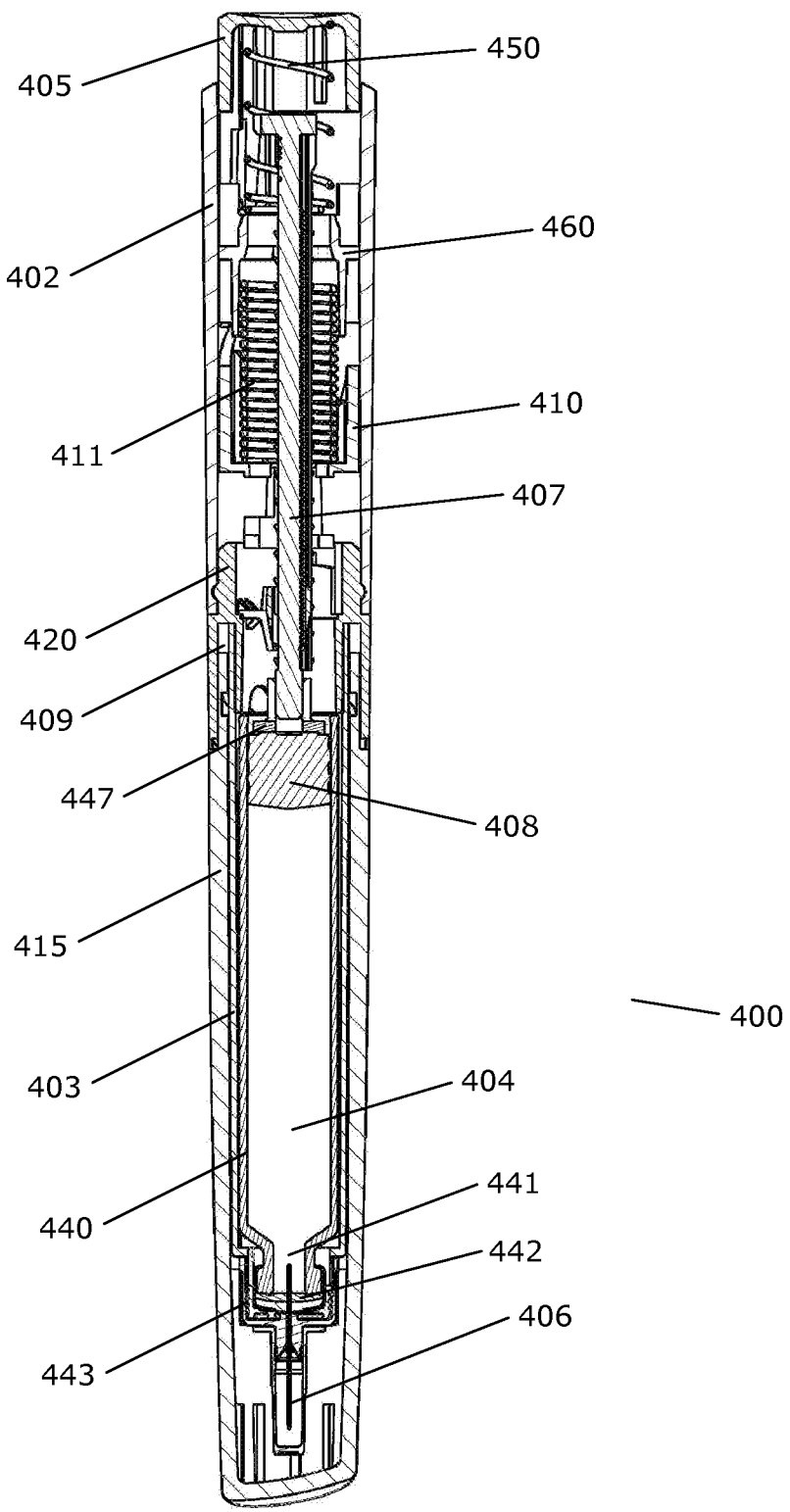
FIG. 21 is a cross sectional view of an injection device according to a fifth embodiment of the invention.

FIG. 21 is a cross sectional view of the injection device 400 which comprises a housing 402, a cartridge 404 containing a liquid drug, a cartridge holding part 403, a cap receiving part 409 and a cap 415. The liquid drug is positioned between a piston 408, which is capable of moving axially in the cartridge 404, a tubular cartridge wall 440, and a self-sealing septum 442 covering a drug outlet 441. An injection needle 406 is attached to the injection device 400 via a needle hub interface 443. An axially moveable piston rod 407 is coupled to the piston 408 via a piston rod foot 447. The piston rod 407 is adapted to be moved axially by a driver 410. A guide member 420 guides the movement of the driver 410 and the piston rod 407. The injection device 400 is powered by a rotationally pre-stressed spring 411 which is locked to the housing 402 at its proximal end, via a spring base 460, and which is coupled to the driver 410 at its distal end. The spring base 460 further holds the distal end of a button spring 450 adapted to bias an injection button 405 towards a position in which it protrudes from the proximal end of the housing 402.

Figure 22:
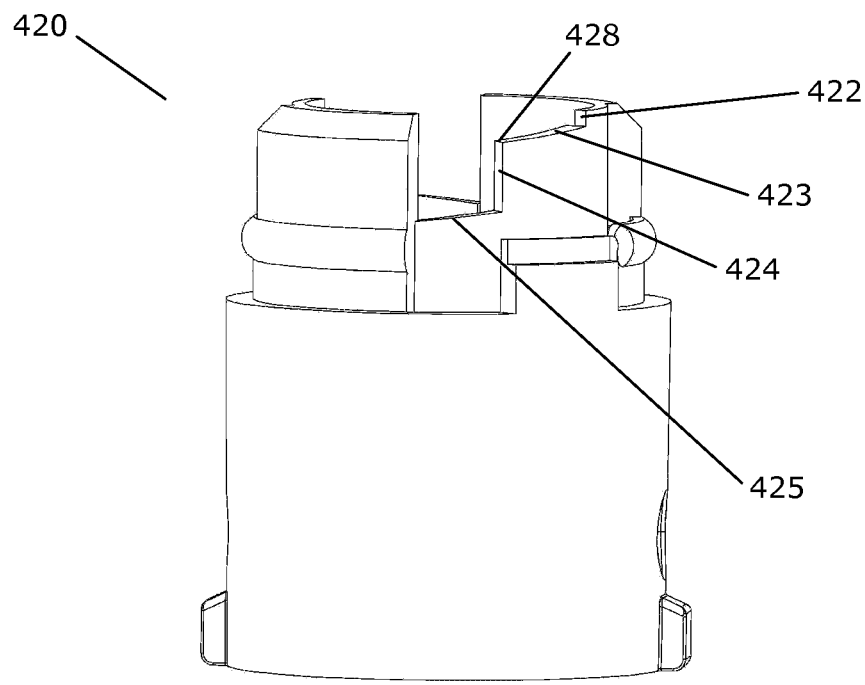
FIG. 22 is a perspective view of a guiding means seen from the side.
Figure 23:
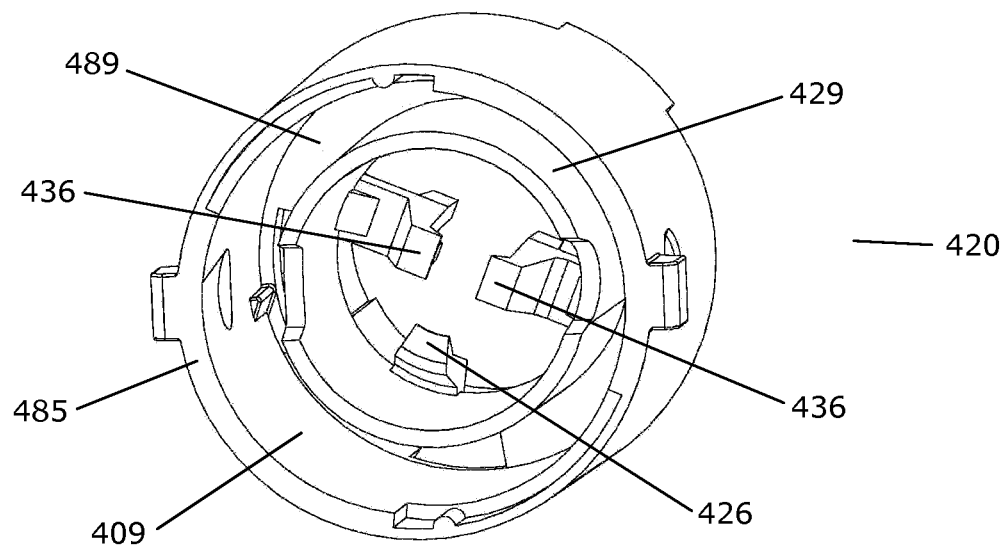
FIG. 23 is a perspective view of a guiding means seen from the distal end.

FIGS. 22 and 23 show the guide member 420 in more detail. The guide member 420 comprises a dose shelf 423 adapted to support and guide the driver 410 during the second part of the dose setting procedure and the first part of the injection procedure. A longitudinal guide surface 424 leads from the dose shelf 423 to an end of dose stop 425. The dose shelf 423 is a helical ramp segment which extends circumferentially from a connection with the longitudinal guide surface 424 to a longitudinal stop surface 422. It is to be understood, that radially opposite this set of guide surfaces is a similar set of guide surfaces. This set is, however, not visible on the figures. A click finger 426 is provided on the guide member 420 for engagement with the piston rod 407. A tubular clearance 489 is provided between an outer wall 429 of an inner tubular structure of the guide member 420 and the wall of the guide member 420. Two radially opposite guide elements 436 are adapted to engage the through-going piston rod 407 (not shown) and guide the axial movements of the piston rod 407 while preventing the piston rod 407 from rotating relative to the housing 402. A distal edge 485 of the guide member 420 is adapted to abut the cap 415 when the cap 415 is engaged in the cap receiving part 409.

FIG. 24 shows the driver 410 which comprises a tubular body 470, a couple of pushing surfaces 469, two slider elements 473 adapted to travel the guide surfaces of the guide member 420, two contact soles 474, and a tooth engaging element 476 adapted to engage with teeth on the piston rod 407 in order to slave the piston rod 407 in a forward motion towards the distal end of the injection device 400. A catch element 475 is further provided for engagement with the proximal end of the piston rod 407 after the last full dose has been delivered from the cartridge 404.

FIG. 25 shows the injection button 405 comprising a push face 452 for interfacing with an operator of the injection device 400. The injection button 405 further has two sets of flanges 453, 455 each provided with pushing surfaces 416 for sliding engagement with the pushing surfaces 469 on the driver 410. The flanges 455 are each provided with a hook 456 adapted to engage with respective catch members (not shown) in the housing 402 for holding the injection button 405 depressed in the housing 402 against the bias of the button spring 450 when the injection mechanism has been activated to inject a set dose. The flanges 453 are each provided with a longitudinal slit 457 adapted to engage with respective protrusions (not shown) in the housing 402 thereby rotationally locking the injection button 405 with respect to the housing 402. The protrusions (not shown) in the housing 402 are capable of axially travelling the slits 457, whereby the injection button 405 is able to move axially relative to the housing 402 a distance determined by the axial dimension of the longitudinal slits 457.

FIG. 26 illustrates the functional connection between the injection button 405 and the driver 410. The shown assembly has been separated from the rest of the injection device for the sake of clarity. When the user depresses the injection button 405 by pushing on the push face 452 the pushing surfaces 416 move into engagement with the pushing surfaces 469 on the driver 410. The purely translational movement of the injection button 405 causes the pushing surfaces 469 to slide along the pushing surfaces 416 whereby the driver 410 is rotated clockwise with respect to the injection button 405 (and the housing 402). In an injection situation this will lead to the tooth engaging element 476 moving into engagement with a tooth on the piston rod 407, and when the slider elements 473 pass the transition point at the ramp edges 428 the spring 411 will force the driver 410, and thereby the tooth engaging element 476 and the piston rod 407, to advance axially in the distal direction to inject the set dose. The interface between the injection button 405 and the driver 410 works both ways, i.e. if the driver 410 is rotated anti-clockwise, e.g. during a dose setting, the pushing surfaces 469 will slide along the pushing surfaces 416 on the flanges 453, 455, whereby the injection button 405 will be released from its retained position and displaced axially out of the housing 402 by the button spring 450.

FIG. 27 depicts the situation where the tooth engaging element 476 has been moved from one tooth 491 to a more proximally positioned tooth 492 during a dose setting. The shown assembly has been separated from the rest of the injection device for the sake of clarity. This has artificially uncovered the proximal spring end 497 which is actually retained in the spring base 460.

FIG. 28 depicts the situation where the slider elements 473 are positioned on the dose shelves 423 at the stop surfaces 422 (not visible) and the injection device is ready for injection. Again the shown assembly has been separated from the rest of the injection device for the sake of clarity. A push on the injection button 405 (not shown) will cause the driver 410 to rotate clockwise (as seen from the injection button) against the rotational bias of the spring 411. At the passage of the ramp edges 428 the slider elements 473 will be forced along the longitudinal guide surfaces 424 towards the end of dose stop 425.

FIG. 29 illustrates an end of content situation. When the last full dose has been delivered from the injection device 400 and the user repositions the cap 415 in the cap receiving part 409 to thereby move the driver 410 proximally in a manner similar to what has previously been described in relation to the injection device 300 the tooth engaging element 476 is moved out of engagement with the most proximal positioned tooth 490 and up along the piston rod 407. This movement is performed synchronously with the movement of the slider elements 473 up along the longitudinal guide surfaces 424. However, as the slider elements 473 approach the transition point at the ramp edges 428, the catch element 475 engages with the stop face 493 and the driver 410 is thereby prevented from rotating with respect to the piston rod 407. Since the piston rod 407 is rotationally locked to the housing 402 the driver 310 is in this particular situation not able to rotate relative to the housing 402. In any previous case, when the user has repositioned the cap 415 in the cap receiving part 409 following an injection and the driver 410 has been moved proximally such that the slider elements 473 have passed the ramp edges 428 and a dose thereby has been set, the last part of the dose setting has been performed automatically by the spring 411 releasing its stored energy for rotational motion of the driver 410. This rotation of the driver 410 has caused a simultaneous translation of the injection button 405 due to the interface between the pushing surfaces 469, 416 deflecting the hooks 456 out of engagement with the catch members (not shown) in the housing 402 thereby releasing the button spring 450 and consequently forcing the injection button 405 out of the housing 402, signalling to the user that a dose has been set and that the device is ready for the next injection.

As the driver 410 is incapable of rotation when the cap 415 is mounted on the injection device 400 after injection of the last full dose, the button spring 450 will not be released and the injection button 405 will therefore not be moved out of the housing 402. This is a signal to the user that the injection device 400 has been emptied.

Figure 30:
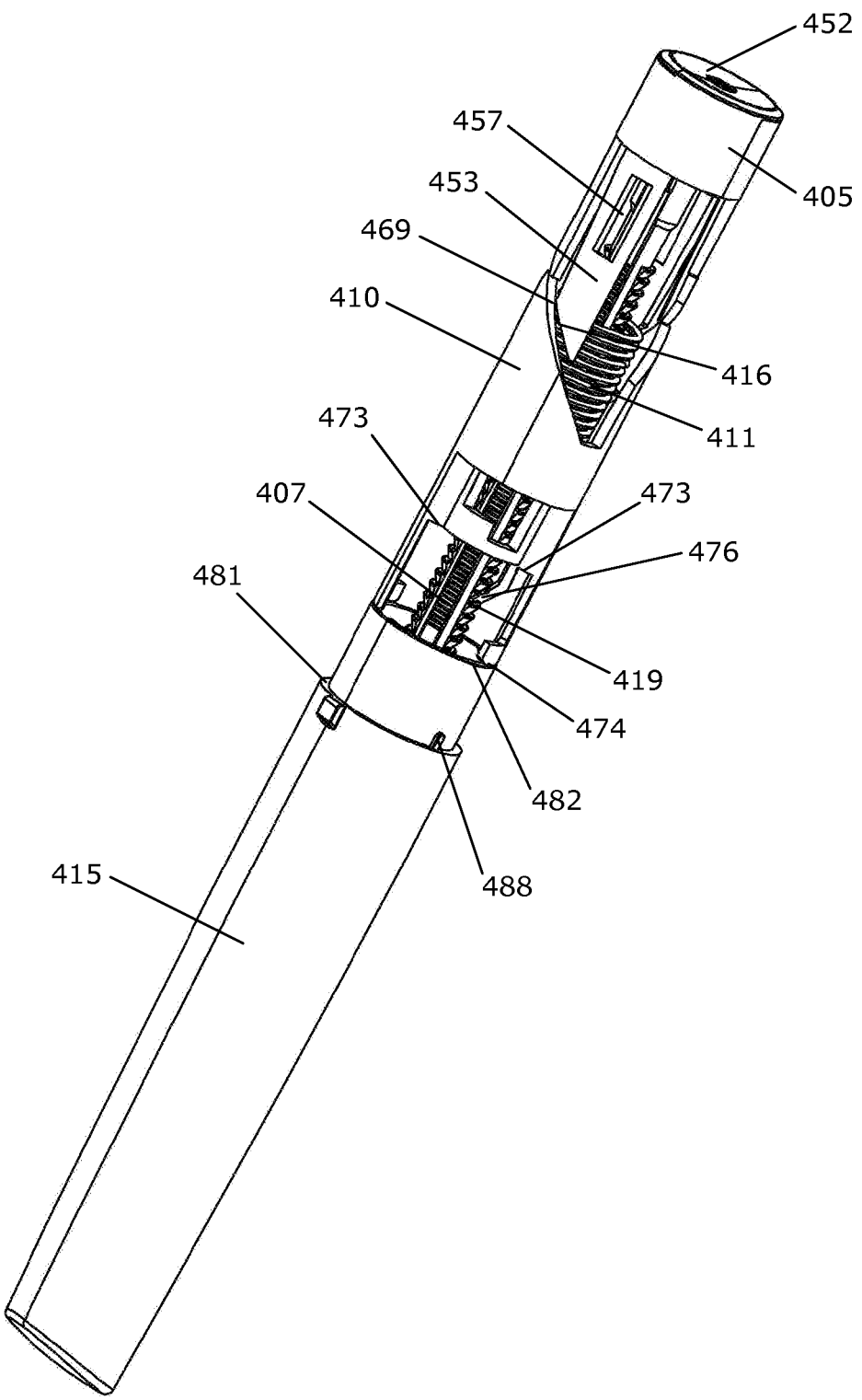
FIG. 30 is a perspective view of the injection device with the housing removed, showing an interaction between the drive member and the protective cap.

FIG. 30 is a perspective view of the injection device 400 with the housing 402 removed, showing an interaction between the driver 410 and the protective cap 415. The figure illustrates a situation where the user tries to eject a dose from the cartridge 404 (not visible) while the cap 415 is mounted on the injection device 400. The basic movement pattern is similar to that described in relation to FIG. 19, the only real difference being the action of the button spring 450 which realises the proximal movement of the injection button 405. A cap edge 482 abuts the contact soles 474 and prevents the driver 410 from undergoing axial displacement towards the distal end of the injection device 400. Depressing the injection button 405 causes the contact soles 474 to slide along the cap edge 482, whereby the tooth engaging element 476 is prevented from moving into contact with a tooth 419 on the piston rod 407. The rotational bias of the spring 411 will pose a return torque on the driver 410 which will again release a locking of the button spring 450 due to the interaction between the pushing surfaces 469 and the flanges 453, 455. When the cap 415 is properly positioned in the cap receiving part 409 an annular abutting surface 481 abuts the distal edge 485 of the guide member 420. A couple of beads 488 on the cap 415 are adapted to engage with a bead receiving track on the inside wall of the guide member 420 for leading the cap 415 properly onto the injection device 400.

Figure 31:
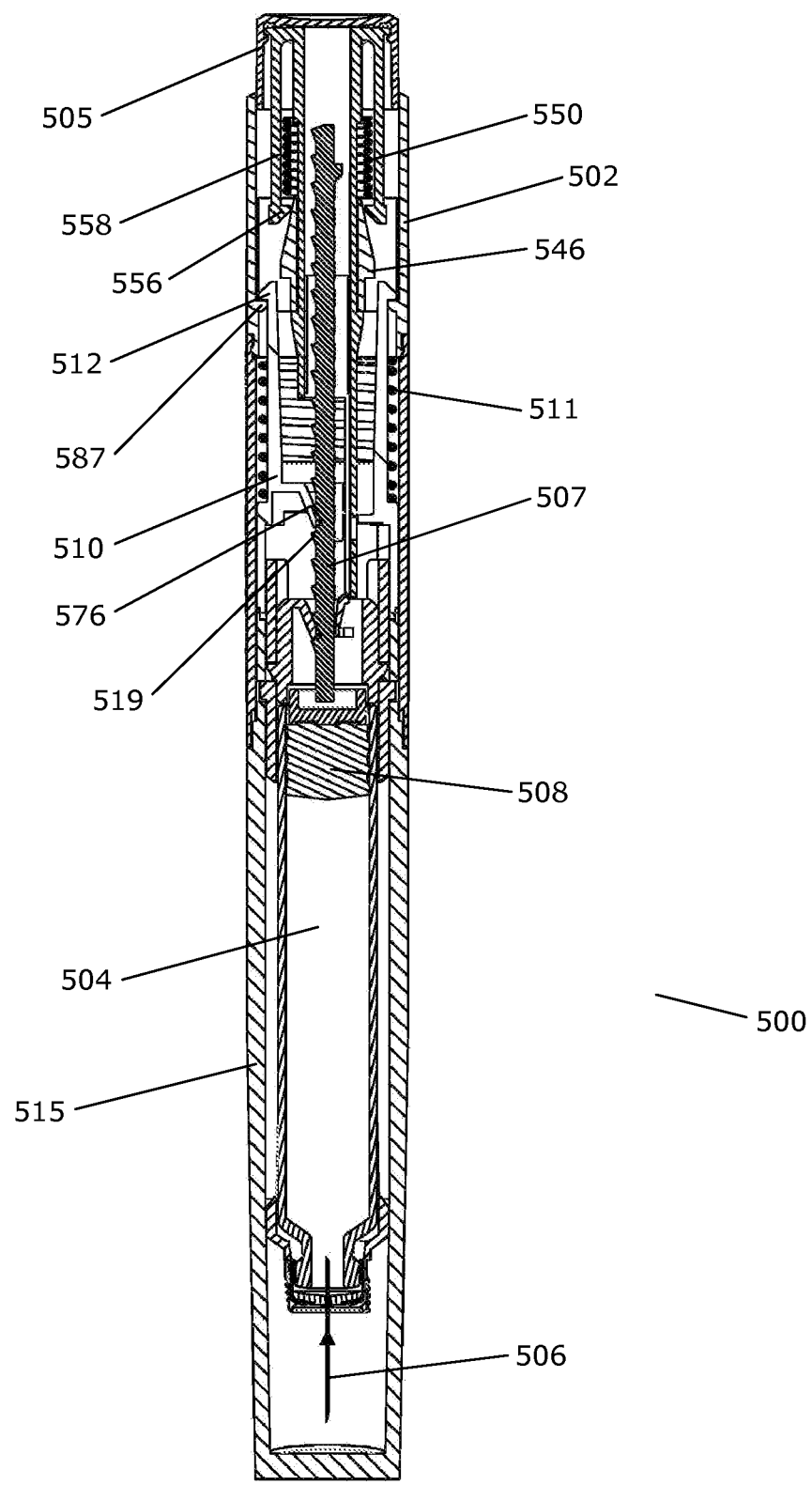
FIG. 31 is a cross sectional view of an injection device according to a sixth embodiment of the invention.

FIG. 31 is a cross sectional view of an injection device 500 according to a sixth embodiment of the invention, in a loaded state, i.e. where a dose is set. The injection device 500 comprises a housing 502, a cartridge 504 with a piston 508, a cap 515, a toothed piston rod 507, a driver 510 comprising a tooth engaging element 576 adapted to engage a tooth 519 on the piston rod 507 and slave the piston rod 507 towards the needle end of the injection device 500. The driver 510 further comprises radially deflectable snap arms 512 adapted to engage with respective protrusions 587 on the housing 502. The snap arms 512 are elastically biased towards the inside wall of the housing 502. A main spring 511 is provided for powering the driver 510 during injection, and a secondary spring 550 is provided for biasing an injection button 505 towards a position in which it protrudes from the proximal end of the housing 502. The injection button 505 has longitudinally extending arms 558 ending in respective hooks 556 adapted to engage with radially protruding catch elements 546 to hold the injection button 505 in a depressed position in the housing 502 against the bias of the secondary spring 550. The injection device 500 further has an injection needle 506 attached.

Figure 32A:
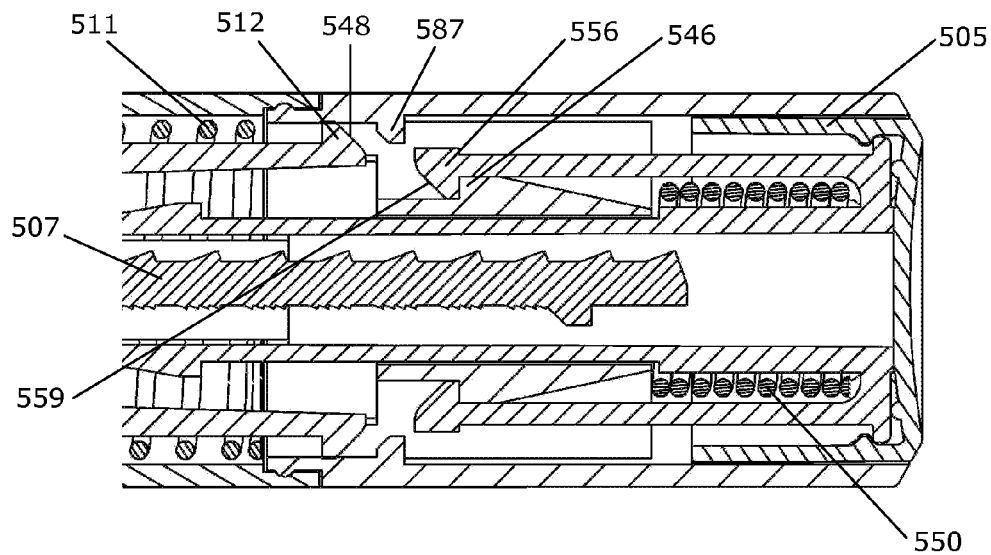
FIGS. 32*a-c* show a push button release mechanism of the injection device in detail.
Figure 32B:
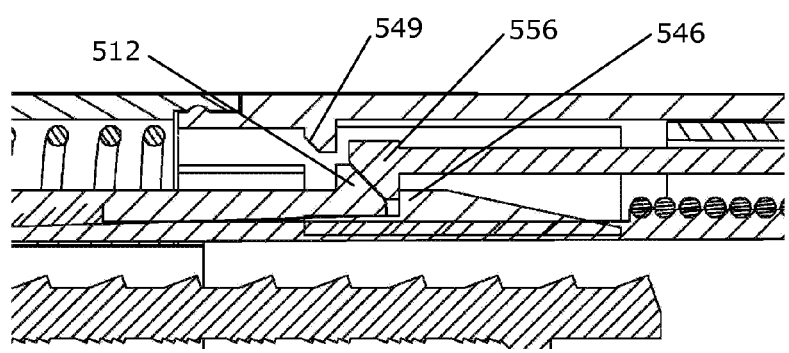
Figure 32C:
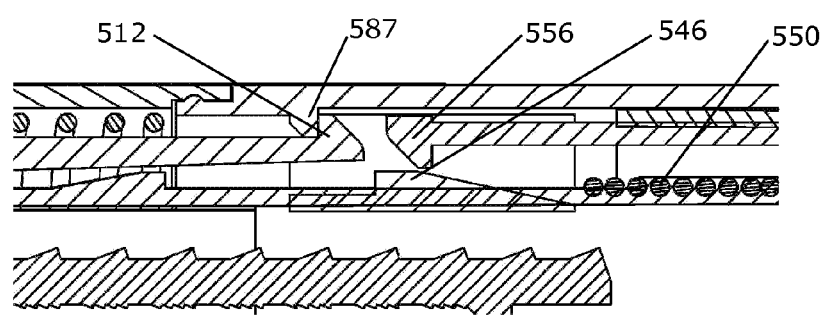

FIGS. 32*a-c* show an injection button release mechanism of the injection device 500 in detail. In FIG. 32*a* the injection button 505 is depressed in the housing 502 illustrating a situation where the user has performed an injection. The injection button 505 is held in this position against the biasing force of the secondary spring 550 due to the engagement between the hooks 556 and the catch elements 546.

In FIG. 32*b* the driver 510 has been displaced proximally in the housing 502 due to the user mounting the cap 515 on the injection device 500. This has caused inclined push faces 548 of the snap arms 512 to slide along corresponding inclined faces 549 of the protrusions 587 and move into contact with corresponding inclined push faces 559 of the hooks 556. Further proximal movement of the driver 510, and thereby the snap arms 512, will cause the inclined push faces 548 of the snap arms 512 to slide along the inclined push faces 559 of the hooks 556, whereby the hooks 556 will be moved out of engagement with the catch elements 546. When the hooks 556 are moved completely out of engagement with the catch elements 546 three things happen simultaneously. The secondary spring 550 releases its stored energy and forces the injection button 505 proximally out of the housing 502, and the snap arms 512 deflect back towards the inside wall of the housing 502 to move into engagement with the proximal faces of the protrusions 587, thereby cocking the main spring 511. This is shown in FIG. 32*c*. Furthermore, the tooth engaging element 576 passes a more proximally positioned tooth 519 on the piston rod 507, whereby a dose is set.

When the user pushes the injection button 505 to inject a set dose the arms 558 are moved distally in the housing 502 while being deflected radially outwards by a sliding engagement with the catch elements 546. The inclined push faces 559 of the hooks 556 are hereby brought into engagement with the inclined push faces 548 of the snap arms 512. As the injection button 505 is being fully depressed against the housing 502 the arms 558 will force the inclined push faces 548 of the snap arms 512 to slide along the inclined push faces 559 of the hooks 556 to a point where the snap arms 512 are moved out of engagement with the protrusions 587. This will cause the main spring 511 to release its stored energy and move the driver 510 distally in the housing 502 to expel the dose of drug through the injection needle 506. Simultaneously, the elastic recovery of the arms 558 will cause the hooks 556 to move into engagement with the catch elements 546, thereby cocking the secondary spring 550 and retaining the injection button 505 within the housing 502.

EXAMPLES

In the following different examples embodying the invention in accordance with the second aspect are presented.
1. An injection device comprising:
    a variable volume reservoir comprising an outlet,
    dose setting means operable to set a dose,
    injection means operable to inject the set dose and comprising an at least partly toothed rod adapted to cause a volume reduction of the reservoir,
    a drive member suited for undergoing relative motion with respect to the toothed rod during dose setting and for transmitting a driving force to the toothed rod during injection, the drive member comprising an engagement element adapted to engage with the toothed rod,
    guiding means adapted to guide the movement of the drive member and/or the toothed rod, and
    energy means operatively coupled to the dose setting means and the injection means and adapted to store and release energy for translational and rotational motion,
    wherein operating the dose setting means to set a dose causes the engagement element to pass a tooth on the toothed rod in a combined translational and rotational movement.
2. An injection device as in example 1, wherein when the dose setting means is operated to set a dose, the energy means releases energy for rotational motion.
3. An injection device as in example 1 or 2, wherein when the dose setting means is operated to set a dose, the energy means stores energy for translational motion.
4. An injection device as in any of the previous examples, wherein when the injection means is operated to inject the set dose, the energy means stores energy for rotational motion.
5. An injection device as in any of the previous examples, wherein when the injection means is operated to inject the set dose, the energy means releases energy for translational motion.
6. An injection device as in any of the previous examples, wherein the guiding means comprises a sloping ramp surface.
7. An injection device as in example 6, wherein the guiding means further comprises a substantially straight longitudinal guiding surface which is connected to the sloping ramp surface at a ramp edge constituting a transition point between a pure translational motion and a combined translational and rotational motion.
8. An injection device as in example 7, wherein the angle between the substantially straight longitudinal guiding surface and the sloping ramp surface lies between 180° and 270°, preferably between 225° and 270°, and more preferably between 240° and 270°.
9. An injection device as in example 7, wherein the drive member is guided by the substantially straight longitudinal guiding surface during a first part of the dose setting and by the sloping ramp surface during a second part of the dose setting.
10. An injection device as in example 9, wherein the second part of the dose setting is performed automatically by the injection device.
11. An injection device as in any of the previous examples, wherein the guiding means comprises a stop for retaining the energy means in a stabile state.
12. An injection device as in any of the previous examples, wherein the energy means comprises a compression spring adapted to be rotationally pre-stressed.
13. An injection device as in any of the previous examples, wherein the energy means comprises a compression spring and a torsion spring.
14. An injection device as in any of the previous examples further comprising a removable cap and a cap receiving part adapted to abut or engage with the cap when the cap is mounted on the injection device, wherein the cap receiving part is operatively coupled with the dose setting means in such a manner that mounting the cap on the injection device operates the dose setting means to set a dose, thereby causing the engagement element to pass a tooth on the toothed rod in a combined translational and rotational movement.
15. An injection device comprising:
    a variable volume reservoir comprising an outlet,
    dose setting means operable to set a dose,
    injection means operable to inject the set dose and comprising an at least partly toothed rod adapted to cause a volume reduction of the reservoir,
    a drive member suited for undergoing relative motion with respect to the toothed rod during dose setting and for transmitting a driving force to the toothed rod during injection, the drive member comprising an engagement element adapted to engage with the toothed rod,
    guiding means adapted to guide the movement of the drive member and/or the toothed rod,
    a push button operatively coupled to the dose setting means and the injection means and adapted to move axially between a first position in which the dose is set and a second position in which the injection means has been activated to inject the set dose, and
    energy means operatively coupled to the dose setting means and the injection means and adapted to store and release energy for translational and rotational motion,
    wherein operating the dose setting means to set a dose causes the engagement element to pass a tooth on the toothed rod in a combined translational and rotational movement,
    the energy means to store energy for translational motion, the energy being releasable only by operation of the injection means, and
    the push button to move from the second position to the first position.
16. An injection device as in example 15 further comprising a removable cap and a cap receiving part adapted to abut or engage with the cap when the cap is mounted on the injection device, wherein the cap receiving part is operatively coupled with the dose setting means in such a manner that mounting the cap on the injection device operates the dose setting means to set a dose.

In the following different examples embodying the invention in accordance with the third aspect are presented.
1. An injection device comprising:
    a variable volume reservoir comprising an outlet,
    dose setting means operable to set a dose,
    injection means operable to inject the set dose and comprising an at least partly toothed rod operatively coupled to the reservoir such that a translational movement of the toothed rod causes a volume reduction of the reservoir,
    a drive member suited for undergoing relative motion with respect to the toothed rod during dose setting and to transmit a driving force to the toothed rod during injection, the drive member comprising an engagement element adapted to engage with the toothed rod, and guiding means adapted to guide the movement of the drive member and/or the toothed rod, wherein the guiding means comprises a first substantially straight longitudinal guiding surface and a second substantially straight longitudinal guiding surface, the second substantially straight longitudinal guiding surface having a smaller longitudinal dimension than the first substantially straight longitudinal guiding surface.

2. An injection device as in example 1, wherein the guiding means further comprises an angled surface connecting the first substantially straight longitudinal guiding surface and the second substantially straight longitudinal guiding surface.

3. An injection device as in example 2, wherein the angled surface comprises a sloping ramp surface.

4. An injection device as in example 2, wherein the angled surface connects with the first substantially straight longitudinal guiding surface and the second substantially straight longitudinal guiding surface at right angles.

5. An injection device as in any of the previous examples, wherein the drive member is guided by the first substantially straight longitudinal guiding surface during injection.

6. An injection device as in any of the previous examples, wherein the guiding means further comprises a resting shelf adapted to support the drive member until the injection means is operated for the first time.

7. An injection device as in example 6, wherein the resting shelf is connected to the second substantially straight longitudinal guiding surface at an edge.

8. An injection device as in example 7, wherein when the injection means is operated for the first time the drive member is moved from an initial position in which it is supported by the resting shelf along the second substantially straight longitudinal guiding surface to a position in which it rests on the angled surface, the drive member thereby displacing the toothed rod axially a distance which is shorter than the distance corresponding to the injection of a set dose.

9. An injection device as in example 8 further comprising energy means operatively coupled to the dose setting means and the injection means and adapted to store and release energy for translational and/or rotational motion.

10. An injection device as in example 9, wherein the very first operation of the injection means causes the energy means to move the drive member from an initial position in which it is supported by the resting shelf along the second substantially straight longitudinal guiding surface to a position in which it rests on the angled surface.

In the following different examples embodying the invention in accordance with the fourth aspect are presented.

1. An injection device for administering apportioned doses of liquid drug, the injection device comprising:
  a housing,
  a reservoir for holding the drug,
  a piston adapted to move axially in the reservoir,
  dose setting means operable to set a dose,
  injection means operable to inject the set dose and comprising a piston rod for sequentially advancing the piston in the reservoir to expel a volume of the liquid drug, each sequential advancement corresponding to the set dose,
  a push button operatively coupled to the dose setting means and the injection means and axially moveable between a first position in which the dose is set and a second position in which the injection means has been activated to inject the set dose, and
  retaining means for holding the push button in the second position when the injection means has been activated to inject the set dose, wherein the retaining means is operatively coupled to the dose setting means in such a way that when the dose setting means is operated to set a dose the retaining means is automatically disabled.

2. An injection device as in example 1, wherein when the dose setting means is operated to set a dose, the push button is automatically moved from the second position to the first position.

3. An injection device as in example 2, wherein the push button is moved from the second position to the first position by a force transmitting member activating the push button via a translational and/or rotational movement.

4. An injection device as in any of the previous examples further comprising energy means acting on the push button to bias the push button towards the first position.

5. An injection device as in example 4, wherein the energy means comprises a spring.

6. An injection device as in any of the previous examples, wherein the movement of the push button from the second position to the first position is purely translational. 7. An injection device as in any of the previous examples, wherein the movement of the push button from the first position to the second position is purely translational.

8. An injection device as in any of the previous examples, wherein the retaining means comprises a snap fit between the push button and the housing.

9. An injection device as in example 8, wherein the push button comprises a catch member adapted to engage with a protuberance on the housing.

10. An injection device as in example 9, wherein the snap fit is disabled by a force transmitting member having an abutment surface adapted to slideably abut with an abutment surface on the catch member to thereby move the catch member out of engagement with the protuberance.

11. An injection device as in example 3, wherein the retaining means comprises a friction fit between the push button and the housing.

12. An injection device as in any of the previous examples further comprising a drive member adapted to undergo relative motion with respect to the piston rod during dose setting and to transmit a driving force to the piston rod during injection, the drive member comprising force transmitting means.

13. An injection device as in example 12, wherein the push button and the drive member are operatively coupled in such a manner that a rotational or spiralling movement of the drive member causes an axial movement of the push button, and vice versa.

14. An injection device as in example 12 or 13 further comprising a coupling element adapted to engage with the drive member and the push button.

15. An injection device as in example 14, wherein the push button and the coupling element are coupled via a threaded interface.

16. An injection device as in example 15, wherein the push button comprises a helical track segment and the coupling element comprises a protuberance adapted to engage with and travel the helical track segment.

17. An injection device as in example 16, wherein the retaining means comprises the engagement between the push button and the coupling element.

18. An injection device as in example 13, wherein the piston rod comprises a structural element adapted to engage with the drive member to prevent the drive member from rotating when the remaining amount of drug in the reservoir is insufficient to provide another full dose, thereby also preventing the dose setting means from setting a dose.

19. An injection device as in example 13, wherein the piston rod comprises a structural element adapted to engage with the drive member to prevent the drive member from rotating when the remaining amount of drug in the reservoir is insufficient to provide another full dose, thereby also preventing movement of the push button from the second position to the first position.

20. An injection device as in any of the previous examples further comprising:
a removable cap, and
a cap receiving part adapted to abut or engage with the cap when the cap is mounted on the injection device,
wherein the cap receiving part is operatively coupled to the dose setting means in such a way that mounting the cap on the injection device automatically disables the retaining means and moves the push button from the second position to the first position.

In the following different examples embodying the invention in accordance with the fifth aspect are presented.

1. An injection device for administering apportioned doses of liquid drug, the injection device comprising:
a reservoir adapted to hold the drug,
a piston adapted to move axially in the reservoir,
dose setting means operable to set a dose,
injection means operable to inject the set dose and comprising a piston rod for sequentially advancing the piston in the reservoir to expel a volume of the liquid drug, each sequential advancement corresponding to the set dose,
a removable cap,
a cap receiving part adapted to abut or engage with the cap when the cap is mounted on the injection device,
wherein the injection means is operatively coupled to the cap receiving part in such a manner that mounting the cap on the injection device disables the injection means, thereby preventing an ejection of drug from the reservoir.

2. An injection device as in example 1, wherein dismounting the cap from the injection device enables the injection means, thereby allowing an ejection of drug from the reservoir.

3. An injection device as in example 1 or 2, wherein the cap is mounted on and/or dismounted from the injection device in a substantially linear movement.

4. An injection device as in any of the previous examples, wherein the cap is mounted on and/or dismounted from the injection device in a rotational or spiralling movement.

5. An injection device as in any of the previous examples, wherein when the cap is mounted on the injection device the piston rod is prevented from axial movement.

6. An injection device as in any of the previous examples further comprising a drive member adapted to transmit a driving force to the piston rod during injection, wherein when the cap is mounted on the injection device the drive member is capable of performing rotational motion, but prevented from performing translational motion, with respect to the cap.

7. An injection device as in example 6, wherein the drive member abuts the cap when the cap is mounted on the injection device.

8. An injection device as in example 6 or 7 further comprising means for holding the cap on the injection device against a translational force from the drive member.

9. An injection device as in example 6 further comprising an injection button operatively coupled to the dose setting means and the injection means and axially moveable between a first position corresponding to a position in which the dose is set and a second position corresponding to a position in which the injection means has been activated to inject the set dose, wherein when the cap is mounted on the injection device the injection button is able to move between the first position and the second position.

10. An injection device as in example 9 further comprising energy means operatively coupled to the dose setting means and the injection means and adapted to store and release energy for translational and rotational motion.

11. An injection device as in example 10, wherein applying a force to move the injection button from the first position to the second position when the cap is mounted on the injection device causes the drive member to rotate while the energy means stores energy for rotational motion.

12. An injection device as in example 11, wherein removing the force from the injection button when the cap is mounted on the injection device causes the drive member to rotate while the energy means releases energy for rotational motion.

13. An injection device as in example 12, wherein the injection button is automatically moved from the second position to the first position when the force is removed.

14. An injection device as in any of the previous examples, wherein the dose setting means is operatively coupled to the cap receiving part in such a manner that mounting the cap on the injection device causes the dose setting means to set a dose.

The invention claimed is:

1. An injection device comprising:
a variable volume reservoir comprising an outlet,
a dose setting assembly,
a removable cap,
a cap receiving part adapted to abut or engage with the cap when the cap is mounted on the injection device, wherein the cap receiving part is operatively coupled to the dose setting assembly, wherein the dose setting assembly is configured to set a dose in response to the cap being mounted on and/or dismounted from the outlet of the injection device,
an injection assembly operable to inject the set dose and comprising an at least partly toothed rod adapted to cause a volume reduction of the reservoir,
a drive member suited for undergoing relative motion with respect to the toothed rod during dose setting and for transmitting a driving force to the toothed rod during injection, the drive member comprising an engagement element adapted to engage with the toothed rod,
a guiding assembly adapted to guide a movement of the drive member and/or the toothed rod, and
an energy assembly operatively coupled to the dose setting assembly and the injection assembly and adapted to store and release energy for translational and rotational motion,
wherein operating the dose setting assembly to set the dose causes the engagement element to pass a tooth on the toothed rod in a combined translational and rotational movement.

2. The injection device as in claim 1, wherein when the dose setting assembly is operated to set the dose, the energy assembly releases the energy for the rotational motion.

3. The injection device as in claim 1, wherein when the dose setting assembly is operated to set the dose, the energy assembly stores the energy for the translational motion.

4. The injection device as in claim 1, wherein when the injection assembly is operated to inject the set dose, the energy assembly stores the energy for the rotational motion.

5. The injection device as in claim 1, wherein when the injection assembly is operated to inject the set dose, the energy assembly releases the energy for the translational motion.

6. The injection device as in claim 1, wherein the guiding assembly comprises a sloping ramp surface.

7. The injection device as in claim 6, wherein the guiding assembly further comprises a substantially straight longitudinal guiding surface which is connected to the sloping ramp surface at a ramp edge constituting a transition point between a pure translational motion and the combined translational and rotational movement.

8. The injection device as in claim 7, wherein an angle between the substantially straight longitudinal guiding surface and the sloping ramp surface lies between 180° and 270°.

9. The injection device as in claim 8, wherein the angle between the substantially straight longitudinal guiding surface and the sloping ramp surface lies between 225° and 270°.

10. The injection device as in claim 9, wherein the angle between the substantially straight longitudinal guiding surface and the sloping ramp surface lies between 240° and 270°.

11. The injection device as in claim 7, wherein the drive member is guided by the substantially straight longitudinal guiding surface during a first part of the dose setting and by the sloping ramp surface during a second part of the dose setting.

12. The injection device as in claim 11, wherein the second part of the dose setting is performed automatically by the injection device.

13. The injection device as in claim 1, wherein the guiding assembly comprises a stop for retaining the energy assembly in a stabile state.

14. The injection device as in claim 1, wherein the energy assembly comprises a compression spring adapted to be rotationally pre-stressed.

15. The injection device as in claim 1, wherein the energy assembly comprises a compression spring and a torsion spring.

16. The injection device as in claim 1, further comprising:
wherein the cap receiving part is operatively coupled to the dose setting assembly in such a way that mounting the cap on the injection device automatically disables a retaining means and moves a push button from a second position to a first position.

17. An injection device comprising:

a variable volume reservoir comprising an outlet, a dose setting assembly, a removable cap, a cap receiving part adapted to abut or engage with the cap when the cap is mounted on the injection device, wherein the cap receiving part is operatively coupled to the dose setting assembly, wherein the dose setting assembly is configured to set a dose in response to the cap being mounted on and/or dismounted from the outlet of the injection device, an injection assembly operable to inject the set dose and comprising an at least partly toothed rod adapted to cause a volume reduction of the reservoir, a drive member suited for undergoing relative motion with respect to the toothed rod during dose setting and for transmitting a driving force to the toothed rod during injection, the drive member comprising an engagement element adapted to engage with the toothed rod, a guiding assembly adapted to guide a movement of the drive member and/or the toothed rod, and a push button operatively coupled to the dose setting assembly and the injection assembly and adapted to move axially between a first position in which the dose is set and a second position in which the injection assembly has been activated to inject the set dose, and an energy assembly operatively coupled to the dose setting assembly and the injection assembly and adapted to store and release energy for translational and rotational motion, wherein operating the dose setting assembly to set the dose causes the engagement element to pass a tooth on the toothed rod in a combined translational and rotational movement the energy assembly to store the energy for the translational motion, the energy being releasable only by operation of the injection assembly, and the push button to move from the second position to the first position.

* * * * *